(12) United States Patent
Howard

(10) Patent No.: US 6,627,627 B2
(45) Date of Patent: Sep. 30, 2003

(54) ARALKYL AND ARALKYLIDENE HETEROCYCLIC LACTAMS AND IMIDES

(75) Inventor: Harry Ralph Howard, Bristol, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/993,741

(22) Filed: Nov. 6, 2001

(65) Prior Publication Data

US 2002/0072519 A1 Jun. 13, 2002

Related U.S. Application Data

(63) Continuation of application No. 09/254,999, filed as application No. PCT/IB97/01062 on Sep. 8, 1997, now Pat. No. 6,380,186.
(60) Provisional application No. 60/027,111, filed on Sep. 30, 1996.
(51) Int. Cl.$^7$ .................... A61K 31/541; C07D 279/12; C07D 295/073; C07D 417/08
(52) U.S. Cl. ................... 514/227.8; 514/235.8; 544/59; 544/60; 558/426
(58) Field of Search ................... 544/59, 60; 514/227.8, 514/235.8; 558/426

(56) References Cited

U.S. PATENT DOCUMENTS 6,380,186 B1 * 4/2002 Howard

* cited by examiner

*Primary Examiner*—Taofiq Solola
(74) *Attorney, Agent, or Firm*—P. C. Richardson; P. H. Ginsburg; A. D. Joran

(57) ABSTRACT

The present invention relates to compounds of the formula

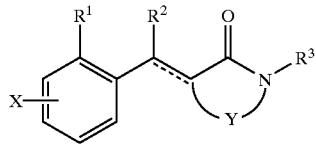

I wherein $R^1$, $R^2$, $R^3$, X, Y and the dashed line are defined as in the specification, to intermediates for their preparation, to pharmaceutical compositions containing them and to their medicinal use. These compounds are useful as psychotherapeutic agents.

5 Claims, No Drawings

ARALKYL AND ARALKYLIDENE HETEROCYCLIC LACTAMS AND IMIDES

This application is a continuation application of U.S. Ser. No. 09/254,999, filed Oct. 8, 1999 now U.S. Pat. No. 6,380,186, which is the Section 371 National Stage of PCT/IB97/01062, filed Sep. 8, 1997, which claims the benefit of U.S. provisional application Ser. No. 60/027,111, filed Sep. 30, 1996.

BACKGROUND OF THE INVENTION

The present invention relates to novel aralkyl and aralkylidene heterocyclic lactams and imides, to intermediates for their preparation, to pharmaceutical compositions containing them and to their medicinal use. The compounds of the present invention include selective agonists and antagonists of serotonin 1 (5-$HT_1$) receptors, specifically, of one or both of the 5-$HT_{1A}$, and 5-$HT_{1D}$ receptors. They are useful in treating or preventing migraine, depression and other disorders for which a 5-$HT_1$ agonist or antagonist is indicated.

European Patent Publication 434,561, published on Jun. 26, 1991, refers to 7-alkyl, alkoxy, and hydroxysubstituted-1-(4-substituted-1-piperazinyl)-naphthalenes. The compounds are referred to as 5-$HT_1$ agonists and antagonists useful for the treatment of migraine, depression, anxiety, schizophrenia, stress and pain.

European Patent Publication 343,050, published on Nov. 23, 1989, refers to 7-unsubstituted, halogenated, and methoxy substituted-1-(4-substituted-1-piperazinyl)-naphthalenes as useful 5-$HT_{1A}$ ligand therapeutics.

PCT publication WO 94/21619, published Sep. 29, 1994, refers to naphthalene derivatives as 5-$HT_1$ agonists and antagonists.

PCT publication WO 96/00720, published Jan. 11, 1996, refers to naphthyl ethers as useful 5-$HT_1$ agonists and antagonists.

European Patent Publication 701,819, published Mar. 20, 1996, refers to the use of 5-$HT_1$ agonists and antagonists in combination with a 5-HT re-uptake inhibitor.

Glennon et al., refers to 7-methoxy-1-(1-piperazinyl)-naphthalene as a useful 5-$HT_1$ ligand in their article "5-$HT_{1D}$ Serotonin Receptors", *Clinical Drug Res. Dev.*, 22, 25–36 (1991).

Glennon's article "Serotonin Receptors: Clinical Implications", *Neuroscience and Behavioral Reviews*, 14, 35–47 (1990), refers to the pharmacological effects associated with serotonin receptors including appetite suppression, thermoregulation, cardiovascular/hypotensive effects, sleep, psychosis, anxiety, depression, nausea, emesis, Alzheimer's disease, Parkinson's disease and Huntington's disease.

World Patent Application WO 95/31988, published Nov. 30, 1995, refers to the use of a 5-$HT_{1D}$ antagonist in combination with a 5-$HT_{1A}$ antagonist to treat CNS disorders such as depression, generalized anxiety, panic disorder, agoraphobia, social phobias, obsessive-compulsive disorder, post-traumatic stress disorder, memory disorders, anorexia nervosa and bulimia nervosa, Parkinson's disease, tardive dyskinesias, endocrine disorders such as hyperprolactinaemia, vasospasm (particularly in the cerebral vasculature) and hypertension, disorders of the gastrointestinal tract where changes in motility and secretion are involved, as well as sexual dysfunction.

G. Maura et al., *J. Neurochem*, 66 (1), 203–209 (1996), have stated that administration of agonists selective for 5-$HT_{1A}$ receptors or for both 5-$HT_{1A}$ and 5-$HT_{1D}$ receptors might represent a great improvement in the treatment of human cerebellar ataxias, a multifaceted syndrome for which no established therapy is available.

European Patent Publication 666,261, published Aug. 9, 1995 refers to thiazine and thiomorpholine derivatives which are claimed to be useful for the treatment of cataracts.

SUMMARY OF THE INVENTION

The present invention relates to compounds of the formula

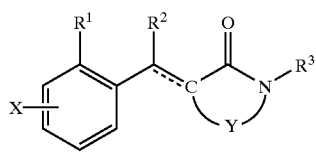

wherein $R^1$ is a group of the formula $G^1$, $G^2$, $G^3$, $G^4$, $G^5$, $G^6$ or $G^7$ depicted below,

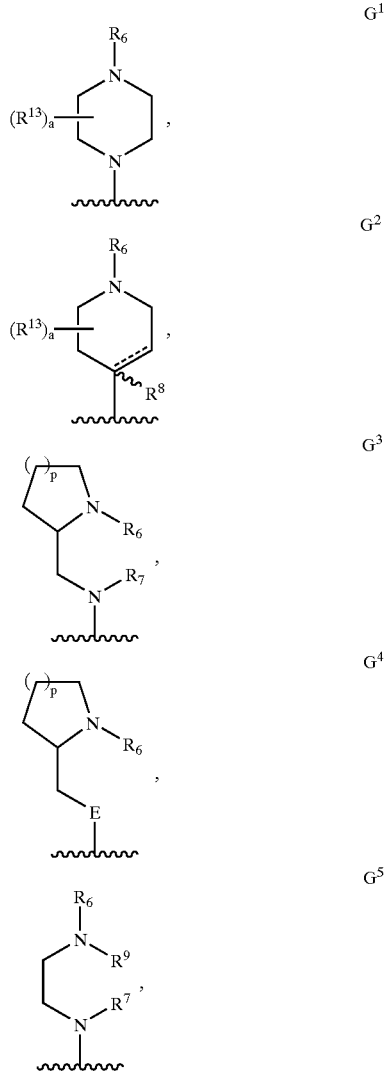

-continued

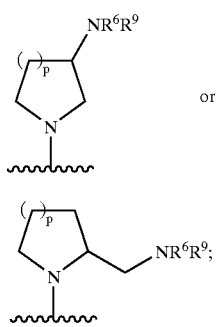

a is zero to eight, each $R^{13}$ is, independently, $(C_1-C_4)$alkyl or a $(C_1-C_4)$ methylene bridge from one of the ring carbons of the piperazine or pipendine ring of $G^1$ or $G^2$, respectively, to the same or another ring carbon or a ring nitrogen of the piperazine or piperidine ring of $G^1$ or $G^2$, respectively, having an available bonding site, or to a ring carbon of $R^6$ having an available bonding site;

E is oxygen, sulfur, SO or $SO_2$;

X is hydrogen, chloro, fluoro, bromo, iodo, cyano, $(C_1-C_6)$alkyl, hydroxy, trifluoromethyl, $(C_1-C_6)$alkoxy, —$SO_t(C_1-C_6)$alkyl wherein t is zero one or two, —$CO_2R^{10}$ or —$CONR^{11}R^{12}$;

Y is an optionally substituted $(C_1-C_4)$ heteroalkyl bridge that, together with the atoms to which it is attached, forms a five to seven membered heterocycle containing two to four heteroatoms selected from the group consisting of 1,3-oxazolidin-4-on-5-yl, 1,3-oxazolidin-2,4-dion-5-yl, 4,5-dihydro-1,2-oxazolidin-3-on-4-yl, 1,3-thiazolidin-4-on-5-yl, 1,3-thiazolidin-2,4-dion-5-yl, 1,3-pyrazolidin-4-on-5-yl, 1,3-imidazolidin-2,4-dion-5-yl, 1,2-pyrazolidin-3-on-4-yl, 1,2-thiazolidin-1,1,3-trion-4-yl, 1,2-thiazolidin-3-on-4-yl, tetrahydro-1,2-oxazin-3-on-4-yl, tetrahydro-1,3-oxazin4-on-5-yl, tetrahydro-1,3-oxazin-2,4-dion-5-yl, morpholin-3-on-2-yl, morpholin-3,5-dion-2-yl, 2,3-dihydro-1,4-oxazin-3-on-2-yl, tetrahydro-1,3-thiazin4-on-5-yl, tetrahydro-1,3-thiazin-2,4-dion-5-yl, tetrahydro-1,2-thiazin-3on-4-yl, thiomorpholin-3-on-2-yl, thiomorpholin-3,5-dion-2-yl, 2,3-dihydro-1,4-thiazin-3-on-2-yl, hexahydro-1,2-diazin-3-on-4-yl, 4,5-dihydro-2H-pyridazin-3-on-4-yl, hexahydro-1,3-diazin4-on-5-yl, hexahydro-1,3-diazin-2,4-dion-5-yl, piperazin-2-on-3-yl, piperazin-2,6-dion-3-yl, tetrahydro-1,3,4-thiadiazin-5-on-6-yl, 5,6-dihydro-1,3,4-thiadiazin-5-on-6-yl, 1,3,4-oxadiazin-5-on-6-yl, 5,6-dihydro-1,2,4-oxadiazin-5-on-6-yl, tetrahydro-1,2,4-oxadiazin-5-on-6-yl, 1,2,4-triazin-5-on-6-yl, tetrahydro-1,2,4-oxadiazin-5-on-6-yl, 5,6-dihydro-1,2,4-oxadiazin-5-on-6-yl, 1,2,4-oxadiazin-3,5-dion-6-yl, 1,2,4-trazin-6-on-5-yl, hexahydro-1,2-oxazepin-3-on-2-yl, hexahydro-1,3-oxazepin-4-on-5-yl, hexahydro-1,4-oxazepin-3-on-2-yl, hexahydro-1,4-oxazepin-3,5-dion-2-yl, hexahydro-1,4-oxazepin-3,5-dion-6-yl, 2,3,5,6-tetrahydro-1,4-oxazepin-5,7-dion-6-yl, hexahydro-1,4-oxazepin-5-on-6-yl, hexahydro-1,3-oxazepin-2,4-dion-5-yl, hexahydro-1,2-thiazepin-3-on-4-yl, hexahydro-1,4-thiazepin-3-on-2-yl, 2,3,4,5-tetrahydro-1,4-thiazepin-3-on-2-yl, hexahydro-1,4-thiazepin-3,5-dion-2-yl, hexahydro-1,4-thiazepin-3,5-dion-6-yl, 2,3,6,7-tetrahydro-1,4-thiazepin-5-on-6-yl, 6,7-dihydro-1,4-thiazepin-5-on-6-yl, hexahydro-1,3-thiazepin-2,4-dion-5-yl, hexahydro-1,2-diazepin-3-on-4-yl, hexahydro-1,3-diazepin-2,4-dion-5-yl, hexahydro-1,4-diazepin-2-on-3-yl, hexahydro-1,4-diazepin-5-on-6-yl, hexahydro-1,4-diazepin-5,7-dion-6-yl, hexahydro-1,3,5-thiadiazepin-3-on-7-yl, 4,5,6,7-tetrahydro-1-3,5-thiadiazepin-6-on-7-yl, and 2,3,5,6-tetrahydro-1,2,4-triazepin-3,5-dion-7-yl; wherein the substituents on any of the carbon atoms capable of supporting an additional bond, of said $(C_1-C_4)$ heteroalkyl bridge, are chloro, fluoro, $(C_1-C_6)$alkyl, $(C_1-C_6)$alkoxy, trifluoromethyl or cyano; wherein the substituents on any of the nitrogen atoms capable of supporting an additional bond, of said $(C_1-C_4)$ heteroalkyl bridge, are $(C_1-C_4)$alkyl or trifluoromethyl;

$R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_4)$alkyl, $(C_1-C_6)$alkoxy, trifluoromethyl, cyano and —$SO_k(C_1-C_6)$alkyl wherein k is zero, one or two;

$R^3$ is —$(CH_2)_mB$, wherein m is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$ alkoxy-$(C_1-C_6)$alkyl-, trifluoromethyl, trifluoromethoxy, cyano, hydroxy, —COOH and —$SO_n(C_1-C_6)$alkyl wherein n is zero, one or two;

$R^6$ is selected from the group consisting of hydrogen, $(C_1-C_6)$alkyl optionally substituted with $(C_1-C_4)$ alkoxy or one to three fluorine atoms, or $[(C_1-C_4)$ alkyl]aryl wherein the aryl moiety is phenyl, naphthyl, or heteroaryl-$(CH_2)_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and $_{SOg}(C_1-C_6)$alkyl, wherein g is zero, one or two;

$R^7$ is selected from the group consisting of hydrogen, $(C_1-C_6)$alkyl, $[(C_1-C_4)$alkyl]aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_4)$alkoxy, trifluoromethyl, —$C(=O)$—$(C_1-C_4)$alkyl, cyano and —$SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^8$ and $R^9$, together with the nitrogen atom to which they are attached, form a 5 to 7 membered heteroalkyl ring that may contain from zero to four heteroatoms selected from nitrogen, sulfur and oxygen;

and p is one, two, or three;

each of $R^{10}$, $R^{11}$ and $R^{12}$ is selected, independently, from the radicals set forth in the definition of $R^2$; or $R^{11}$ and $R^{12}$, together with the nitrogen to which they are attached, form a 5 to 7 membered heteroalkyl ring that may contain from zero to four heteroatoms selected from nitrogen, sulfur and oxygen; and the broken lines indicate optional double bonds, with the proviso that when the broken line in $G^2$ is a double bond that $R^8$ is absent;

or a pharmaceutically acceptable salt thereof.

The following are more specific embodiments of groups $G^1$ and $G^2$.

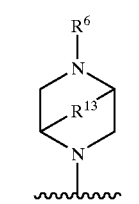
G¹-a

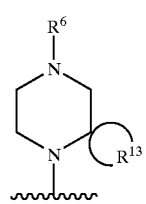
G¹-b

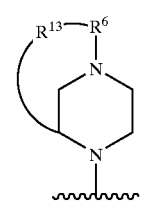
G¹-c

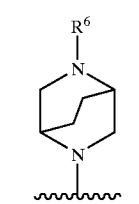
G¹-d

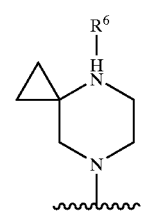
G¹-e

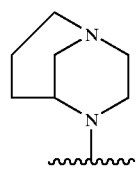
G¹-f

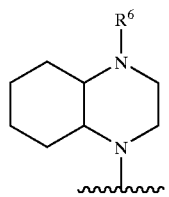
G¹-g

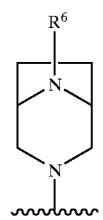
G¹-h

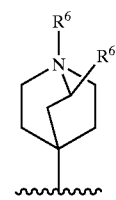
G²-a

The present invention relates to the pharmaceutically acceptable acid addition salts of the compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.q., potassium and sodium) and alkaline earth metal cations (e.q., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds of this invention may contain olefin-like double bonds. When such bonds are present, the compounds of the invention exist as cis and trans configurations and as mixtures thereof.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties. Unless otherwise indicated, halogen includes fluorine, chlorine, bromine, and iodine.

Preferred compounds of the formula I include those wherein $R^1$ is

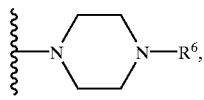

$R^6$ is methyl and $R^2$ is hydrogen.

Preferred compounds of the formula I also include those wherein Y, together with the atoms to which it is attached, forms an optionally substituted five to seven membered heterocycle selected from 1,3 thiazolidin-2,4-dion-5-yl, 1,3 imidazolidin-2,4-dion-5-yl, thiomorpholin-3-on-2-yl or morpholin-3-on-2-yl.

Preferred compounds of the formula I also include those wherein $R^3$ is optionally substituted phenyl or —(CH$_2$)- optionally substituted phenyl.

Examples of specific preferred compounds of the formula I are the following:

3-(4-chlorophenyl)-5-[2-(4-methylpiperazin-1-yl)-benzylidene]-imidazolidine-2,4-dione;

3-(4-chlorobenzyl)-5-[2-(4-methylpiperazin-1-yl)-benzylidene]-imidazolidine-2,4-dione;

3-(4-chlorobenzyl)-5-[2-(4-methylpiperazin-1-yl)-benzylidene]-thiazolidine-2,4-dione;

4-benzyl-2-[2-(4-methylpiperazin-1-yl)-benzylidene]-thiomorpholin-3-one, 4-(3,4-dichlorobenzyl)-2-[2-(4-methylpiperazin-1-yl)-benzylidenepthiomorpholin-3-one;

3-(4-chlorophenyl)-5-[2-(4-methylpiperazin-1-yl)-benzylidene]-thiazolidine-2,4-dione;

3-(4-trifluoromethylphenyl)-5-[2-(4-methylpiperazin-1-yl)-benzylidene]-thiazolidine-2,4-dione;

2-[2-(4-methylpiperazin-1-yl)-benzylidene]-4-(4-trifluoromethylphenyl)-thiomorpholin-3-one;

2-[2-(4-methylpiperazin-1-yl)-benzylidene]-thiomorpholin-3-one;

4-(3,4-dichlorophenyl)-2-[2-fluoro-6-(4-methylpiperazin-1-yl)-benzylidene]-thiomorpholin-3-one;

4-(3,4-dichlorophenyl)-2-[2-(4-methylpiperazin-1-yl)-benzylidene]-morpholin-3-one;

4-(3,4-dichlorophenyl)-2-[2-(4-methylpiperazin-1-yl)-benzylidene]-thiomorpholin-3-one;

4-(3,4-dichlorophenyl)-2-[2-(4-methylpiperazin-1-yl)-benzyl]-thiomorpholin-3-one;

4-methyl-2-[2-(4-methylpiperazin-1-yl)-benzylidene]-thiomorpholin-3-one; and 4-(3,4-dichlorophenyl)-2-(2-piperazin-1-yl-benzylidene)-thiomorpholin-3-one.

4-Benzyl-2-[2-(4-methylpiperazin-1-yl)-benzylidene]-1,1-dioxothiomorpholin-3-one;

4-(3,4-Dichlorophenyl)-2-[3-fluoro-2-(4-methylpiperazin-1-yl)-benzylidene]-thiomorpholin-3-one;

4-(3,4-Dichlorophenyl)-2-[5-fluoro-2-(4-methylpiperazin-1-yl)-benzylidene]-thiomorpholin-3-one;

4-(3,4-Dichlorophenyl)-2-[2-(4-methylpiperazin-1-yl)-5-trifluoromethyl-benzylidene]-thiomorpholin-3-one;

4-(3,4-Dichlorophenyl)-2-{2-[4-(2-methoxyethyl)piperazin-1-yl]-benzylidene}-thiomorpholin-3-one;

4-(3,4-Dichlorophenyl)-2-[2-(4-isopropylpiperazin-1-yl)-benzylidene]-thiomorpholin-3-one;

4-(3,4-Dichlorophenyl)-2-[2-(4-ethylpiperazin-1-yl)-benzylidene]-thiomorpholin-3-one;

4-(4-Chlorophenyl)-2-[2-(4-methylpiperazin-1-yl)-benzylidene]-thiomorpholin-3-one;

4-(3-Chlorophenyl)-2-[2-(4-methylpiperazin-1-yl)-benzylidene]-thiomorpholin-3-one;

2-[2-Chloro-6-(4-methylpiperazin-1-yl)-benzylidene]-4-(3,4-dichlorophenyl)-thiomorpholin-3-one;

4-(3,4-Dichlorophenyl)-2-[2-(4-methylpiperazin-1-yl)-4-trifluoromethyl-benzylidene]-thiomorpholin-3-one;

4-(3,4-Dichlorophenyl)-2-[2-(4-methylpiperazin-1-yl)-benzylidene]-1-oxo-thiomorpholin-3-one;

4-(3,4-Dichlorophenyl)-2-(5-fluoro-2-piperazin-1-yl-benzylidene)-thiomorpholin-3-one;

4-(3,4-Dichlorophenyl)-2-[3,6-difluoro-2-(4-methylpiperazin-1-yl)-benzylidene]-thiomorpholin-3-one;

4-(3,4-Dichlorophenyl)-2-[2-(3,5-dimethylpiperazin-1-yl)-benzylidene]-thiomorpholin-3-one;

4-Phenyl-2-[2-(3,4,5-trimethylpiperazin-1-yl)-benzylidene]-thiomorpholin-3-one;

2-[5-Fluoro-2-(4-methylpiperazin-1-yl)-benzylidene]-4-phenyl-thiomorpholin-3-one;

4-Benzo[1,3]dioxol-5-yl-2-[2-(3,5-dimethylpiperazin-1-yl)-benzylidene]-thiomorpholin-3-one;

2-[2-(4-tert-Butylpiperazin-1-yl)-benzylidene]-4-(3,4-dichlorophenyl)-thiomorpholin-3-one;

3-(3,4-Dichlorophenyl)-5-[2-(4-methylpiperazin-1-yl)-benzylidene]-thiazolidin-4-one;

3-[4-(3,4-Dichlorophenyl)-3-oxo-thiomorpholin-2-ylidenemethyl]-6-dimethylamino-2-(4-methylpiperazin-1-yl)-benzonitrile;

5-[2-(4-Methylpiperazin-1-yl)-benzylidene]-2-phenylthiazolidin-4-one;

4-(3,4-Dichlorophenyl)-2-[2-(3,4,5-trimethylpiperazin-1-yl)-benzylidene]-thiomorpholin-3-one;

4-(3,4-Dichlorophenyl)-2-[5-methyl-2-(4-methylpiperazin-1-yl)-benzylidene]-thiomorpholin-3-one;

2-[4-Chloro-2-(4-methylpiperazin-1-yl)-benzylidene]-4-(3,4-dichlorophenyl)-thiomorpholin-3-one;

4-(3,4-Difluorophenyl)-2-[2-(3,5-dimethylpiperazin-1-yl)-benzylidene]-thiomorpholin-3-one;

4-(2,4-Difluorophenyl)-2-[2-(3,5-dimethylpiperazin-1-yl)-benzylidene]-thiomorpholin-3-one;

2-[4-Bromo-2-(4-methylpiperazin-1-yl)-benzylidene]-4-(3,4-dichlorophenyl)-thiomorpholin-3-one;

4-(3,4-Dichlorophenyl)-2-[2-(1-methylpyrrolidin-2-ylmethoxy)-benzylidene]-thiomorpholin-3-one;

4-(3,5-Dichlorophenyl)-2-[2-(3,5-dimethylpiperazin-1-yl)-benzylidene]-thiomorpholin-3-one;

4-(3,4-Difluorophenyl)-2-[2-(3,4,5-trimethylpiperazin-1-yl)-benzylidene]-thiomorpholin-3-one;

4-(3,4-Dichlorophenyl)-2-[2-(octahydropyrido[1,2-a]pyrazin-2-yl)-benzylidene]-thiomorpholin-3-one;

2-[2-(4-Cyclopropylpiperazin-1-yl)-benzylidene]-4-pyridin-3-yl-thiomorpholin-3-one;

2-[2-(4-Cyclopropylpiperazin-1-yl)-benzylidene]-4-(3,4-difluorophenyl)-thiomorpholin-3-one;

2-[2-(4-Cyclopropylpiperazin-1-yl)-benzylidene]-4-(3,5-dichlorophenyl)-thiomorpholin-3-one;

4-(3,4-Difluorophenyl)-2-[2-(2,5-dimethylpiperazin-1-yl)-benzylidene]-thiomorpholin-3-one;

4-(3,5-Dichlorophenyl)-2-[2-(2,5-dimethylpiperazin-1-yl)-benzylidene]-thiomorpholin-3-one;

4-(3,4-Dichlorophenyl)-2-[2-(3-methylaminopyrrolidin-1-yl)-benzylidene]-thiomorpholin-3-one;

4-(3,4-Difluorophenyl)-2-[2-(2,4,5-trimethylpiperazin-1-yl)-benzylidene]-thiomorpholin-3-one;

4-Benzo[1,3]dioxol-5-yl-2-[2-(4-cyclopropylpiperazin-1-yl)-benzylidene]-thiomorpholin-3-one;

2-[2-(3,5-Dimethylpiperazin-1-yl)-benzylidene]4-(4-fluorophenyl)-thiomorpholin-3-one;

4-Benzo[1,3]dioxol-5-yl-2-[2-(2,5-dimethylpiperazin-1-yl)-benzylidene]-thiomorpholin-3-one;

2-[2-(3,5-Dimethylpiperazin-1-yl)-benzylidene]-4-phenylthiomorpholin-3-one;

4-(3,4-Dichlorophenyl)-2-[2-(4-methylpiperazin-1-yl)-benzylidene]-thiomorpholin-3-one;

4-(3,4-Dichlorophenyl)-2-[2-(3-dimethylaminopyrrolidin-1-yl)-benzylidene]-thiomorpholin-3-one;

4-(3,4-Dichlorophenyl)-2-[2-(3-dimethylaminopyrrolidin-1-yl)-benzylidene]-thiomorpholin-3-one;

4-(3,4-Dichlorophenyl)-2-[2-(4-methyl-[1,4]diazepan-1-yl)-benzylidene]-thiomorpholin-3-one;

4-(3,4-Dichlorophenyl)-2-[2-(2,4,6-trimethylpiperazin-1-yl)-benzylidene]-thiomorpholin-3-one; and 2-[2-(4-Cyclopropylpiperazin-1-yl)-benzylidene]-4-(3,4-dichlorophenyl)-thiomorpholin-3-one;

and the pharmaceutically acceptable salts of such compounds.

Other compounds of formula I include the following:

5-[2-(4-methylpiperazin-1-yl)-benzylidene]-thiazolidine-2,4-dione;

2-[2,4-dibromo-6-(4-methylpiperazin-1-yl)-benzylidene]-4-(3,4-dichlorophenyl)-thiomorpholin-3-one;

4-(4-chlorophenyl)-2-[2-(4-methylpiperazin-1-yl)-benzylidene]-[1,4]oxazepan-3-one;

4-(4-chlorophenyl)-2-[2-(4-methylpiperazin-1-yl)-benzylidene]-[1,4,5]oxadiazepan-3-one;

4-(4-chlorophenyl)-2-[2-(4-methylpiperazin-1-yl)-benzylidene]-[1,4]thiazepan-3-one;

4-(3,4-dichlorophenyl)-2-{2-[(2-dimethylaminoethyl)-methyl-amino]-benzylidene}-thiomorpholin-3-one;

4-(3,4-dichlorophenyl)-2-[2-(1-methylpiperidin-4-yl)-benzylidene]thiomorpholin-3-one;

4-(3,4-dichlorophenyl)-2-[2-(1,4-dimethylpiperidin-4-yl)-benzylidene]-thiomorpholin-3one;

4-(3,4-dichlorophenyl)-2-[2-(4-methylpiperazin-1-yl)-benzylidene]-thiomorpholine-3,5-dione;

4-(3,4-dichlorophenyl)-2-[2-(2-dimethylaminoethoxy)-benzylidene]-thiomorpholin-3-one;

4-(3,4-dichlorophenyl)-2-[2-(4-isopropylpiperazin-1-yl)-benzylidene]-thiomorpholin-3-one;

4-(3,4-dichlorophenyl)-2-[2-(1-methylpyrrolidin-3-ylmethyl)-benzylidene]-thiomorpholin-3-one;

4-(3,4-dichlorophenyl)-2-{2-[methyl-(1-methylpyrrolidin-2-ylmethyl)-amino]-benzylidene}-thiomorpholin-3-one;

4-(3,4-dichlorophenyl)-2-[2-(1-methylpyrrolidin-2-ylmethoxy)-benzylidene]-thiomorpholin-3-one;

4-(3,4-dichlorophenyl)-2-{2-[2-(1-methylpyrrolidin-2-yl)-ethyl]-benzylidene}-thiomorpholin-3-one;

1-(3,4-dichlorophenyl)-4-methyl-3-[2-(4-methylpiperazin-1-yl)-benzylidene]-piperazin-2-one;

4-methyl-3-[2-(4-methylpiperazin-1-yl)-benzylidene]-1-(4-trifluoromethylphenyl)-piperazin-2-one;

1-(4-chlorophenyl)-4-methyl-3-[2-(4-methylpiperazin-1-yl)-benzylidene]-piperazin-2-one;

2-[2-(4-methylpiperazin-1-yl)-benzylidene]-4-(4-trifluoromethylphenyl)-morpholin-3-one;

2-[4-fluoro-2-(4-methylpiperazin-1-yl)-benzylidene]-4-(4-trifluoromethylpheriyl)-thiomorpholin-3-one;

2-[5-fluoro-2-(4-methylpiperazin-1-yl)-benzylidene]-4-(4-triflubromethylphenyl)-thiomorpholin-3-one;

2-{1-[2-(4-methylpiperazin-1-yl)-phenyl]-ethylidene}-4-(4-trifluoromethylphenyl)-thiomorpholin-3-one;

2-[2-(4-methylpiperazin-1-yl)-benzyl]-4-(4-triftuoromethylphenyl)-thiomorpholin-3-one;

4-(4-chlorophenyl)-6-methyl-2-[2-(4-methylpiperazin-1-yl)-benzylidene]-thiomorpholin-3-one;

3-(4-chlorophenyl)-2,2-dimethyl-5-[2-(4-methylpiperazin-1-yl)-benzylidene]-thiazolidin-4-one;

4-(4-chlorophenyl)-2-[2-(4-methylpiperazin-1-yl)-benzylidene]-[1,4]oxazepan-3-one;

4-(4-chlorophenyl)-2-[2-(4-methylpiperazin-1-yl)-benzylidene]-4H-[1,4]thiazin-3-one;

1-(4-chlorophenyl)-4,6,6-trimethyl-3-[2-(4-methylpiperazin-1-yl)-benzylidene]-piperazin-2-one;

1-(4-chlorophenyl)4-methyl-3-[2-(4-methylpiperazin-1-yl)-benzylidene]-piperazin-2-one;

4-(4-chlorophenyl)-2-[2-(4-methylpiperazin-1-yl)-benzylidene]-morpholin-3-one;

3-(4-chlorophenyl)-5-[2-(4-methylpiperazin-1-yl)-benzylidene]-oxazolidin-4-one;

3-(4-chlorophenyl)-2,2-dimethyl-5-[2-(4-methylpiperazin-1-yl)-benzylidene-imidazolidin-4-one; and 3-(4-chlorophenyl)-5-[2-(4-methylpiperazin-1-yl)-benzylidene]-imidazolidin-4-one.

The present invention also relates to intermediates of the formula

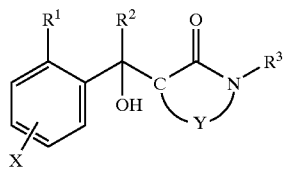

wherein $R^1$—$R^3$, $R^6$—$R^{13}$, $G^7$—$G^5$, X, B, E, Y, Z, g, j, k, m, n, p, q, r and t are as defined above.

Examples of specific preferred compounds of formula V are the following:

4-benzyl-2-{hydroxy-[2-(4-methylpiperazin-1-yl)-phenyl]methyl}-thiomorpholin-3-one;

4-(3,4-dichlorobenzyl)-2-{hydroxy-[2-(4-methylpiperazin-1-yl)-phenyl]methyl}-thiomorpholin-3-one;

2-{hydroxy-[2-(4-methylpiperazin-1-yl)-phenyl] methyl}-4(4-trifluoromethylphenyl)-thiomorpholin-3-one;

2-{hydroxy-[2-(4-methylpiperazin-1-yl)-phenyl] methyl}-thiomorpholin-3-one;

4-(3,4-dichlorophenyl)-2-{[2-fluoro-6-(4-methylpiperazin-1-yl)-phenyl]-hydroxymethyl}-thiomorpholin-3-one;

4-(3,4-dichlorophenyl)-2-{hydroxy-[2-(4-methylpiperazin-1-yl)-phenyl]-methyl}-morpholin-3-one;

2-{[2,4-dibromo-6-(4-methylpiperazin-1-yl)-phenyl]-hydroxymethyl}-4-(3,4-dichlorophenyl)-thiomorpholin-3-one; and 4-(3,4-dichlorophenyl)-2-{hydroxy-[2-(4-methylpiperazin-1-yl)-phenyl]-methyl}-thiomorpholin-3-one.

The present invention also relates to a pharmaceutical composition for treating or preventing a disorder or condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer, (e.g., small cell lung carcinoma), chronic paroxysmal hemicrania and headache (associated with vascular disorders) in a mammal, preferably a human, comprising an amount of a compound of the formula I or a pharmaceutically acceptable salt thereof effective in treating or preventing such disorder or condition and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising an amount of a compound of the formula I, or a pharmaceutically acceptable salt thereof, effective in treating or preventing such disorder or condition and a pharmaceutically acceptable carrier. Examples of such disorders and conditions are those enumerated in the preceding paragraph.

The present invention also relates to a method for treating or preventing a disorder or condition selected from hypertension, depression (e.g., depression in cancer patients, depression in Parkinson's patients, Postmyocardial Infarction depression, Subsyndromal Symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer, (e.g., small cell lung carcinoma), chronic paroxysmal hemicrania and headache (associated with vascular disorders) in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal in need of such treatment or prevention an amount of a compound of the formula I, or a pharmaceutically acceptable salt thereof, that is effective in treating or preventing such disorder or condition.

The present invention also relates to a pharmaceutical composition for treating or preventing a disorder or condition selected from hypertension, depression (e.g., depression in cancer patients, depression in Parkinson's patients, Postmyocardial Infarction depression, Subsyndromal Symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer (e.g., small cell lung carcinoma), chronic paroxysmal hemicrania and headache (associated with vascular disorders) in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a pharmaceutical composition for treating or preventing a disorder or condition that can be treated or prevented by enhancing serotonergic neurotransmission in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a method for treating or preventing a disorder or condition selected from hypertension, depression (e.g., depression in cancer patients, depression in Parkinson's patients, Postmyocardial Infarction depression, Subsyndromal Symptomatic depression, depression in infertile women, pediatric depression, major depression, single episode depression, recurrent depression, child abuse induced depression, and post partum depression), generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer (e.g., small cell lung carcinoma), chronic paroxysmal hemicrania and headache (associated with vascular disorders) in a mammal, preferably a human, comprising administering to a mammal requiring such treatment or prevention a serotonin receptor antagonizing or agonizing effective amount of a compound of the formula I or a pharmaceutically acceptable salt thereof.

The present invention also relates to a method for treating or preventing a disorder or condition that can be treated or prevented by enhancing serotonergic neurotransmission in a mammal, preferably a human, comprising administering to a mammal requiring such treatment or prevention a serotonin receptor antagonizing or agonizing effective amount of a compound of the formula I or a pharmaceutically acceptable salt thereof.

The present invention relates to a pharmaceutical composition for treating or preventing a condition or disorder that can be treated or prevented by enhancing serotonergic neurotransmission in a mammal, preferably a human, comprising:

a) a pharmaceutically acceptable carrier;
b) a compound of the formula I or a pharmaceutically acceptable salt thereof; and
c) a 5-HT re-uptake inhibitor, preferably sertraline, or a pharmaceutically acceptable salt thereof;
    wherein the amount of the active compounds (i.e., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to a mammal requiring such treatment or prevention:

a) a compound of the formula I, defined above, or a pharmaceutically acceptable salt thereof; and
b) a 5-HT re-uptake inhibitor, preferably sertraline, or a pharmaceutically acceptable salt thereof;
    wherein the amounts of the active compounds (e.g., the compound of formula I and the 5-HT re-uptake inhibitor) are such that the combination is effective in treating or preventing such disorder or condition.

The present invention also relates to a method for treating or preventing a disorder or condition that can be treated or prevented by enhancing serotonergic neurotransmission in a mammal, preferably a human, comprising administering to said mammal requiring such treatment or prevention:

a) a $5\text{-HT}_{1A}$ antagonist or a pharmaceutically acceptable salt thereof; and
b) a $5\text{-HT}_{1D}$ antagonist of formula I or a pharmaceutically acceptable salt thereof;
    wherein the amounts of each active compound (i.e., the $5\text{-HT}_{1A}$ antagonist and the $5\text{-HT}_{1D}$ antagonist) are such that the combination is effective in treating or preventing such disorder or condition.

The present invention also relates to a pharmaceutical composition for treating or preventing a disorder or condition that can be treated or prevented by enhancing serotonergic neurotransmission in a mammal, preferably a human, comprising:

a) a $5\text{-HT}_{1A}$ antagonist or a pharmaceutically acceptable salt thereof; and
b) a $5\text{-HT}_{1D}$ antagonist of formula I or a pharmaceutically acceptable salt thereof;
    wherein the amounts of each active compound (i.e., the $5\text{-HT}_{1A}$ antagonist and the $5\text{-HT}_{1D}$ antagonist) are such that the combination is effective in treating or preventing such disorder or condition.

"Enhanced serotonergic neurotransmission," as used herein, refers to increasing or improving the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Valium (trademark)). "Treating a chemical dependency," as used herein, means reducing or alleviating such dependency.

Sertraline, (1S-cis)-4-(3,4-dichlorophenyl)-1,2,3,4-tetrahydro-N-methyl-1-naphthalenamine, as used herein has the chemical formula $C_{17}H_{17}NCl_2$ and the following structural formula

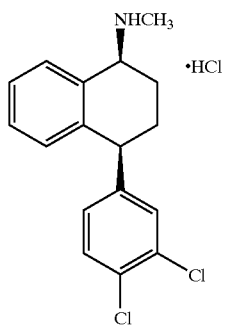

Its synthesis is described in U.S. Pat. No. 4,536,518, assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation.

DETAILED DESCRIPTION OF THE INVENTION

Compounds of the formula I may be prepared according to the following reaction schemes and discussion. Unless otherwise indicated, $R^1$ through $R^3$, $R^6$ through $R^{13}$, $G^1$ through $G^7$, X, B, E, Y, Z, g, j, k, m, n, p, q, r and t and structural formula I in the reaction schemes and discussion that follow are as defined above.

Scheme 1

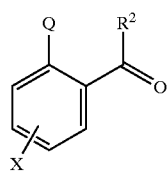

III

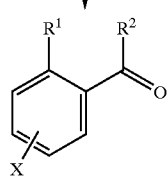

II

-continued

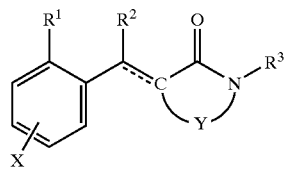

I

Scheme 2

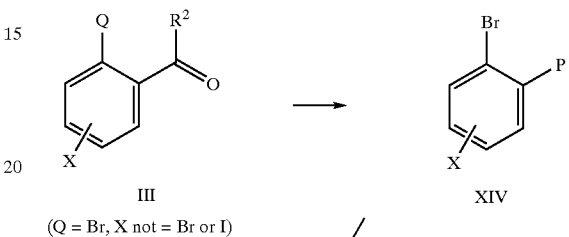

III
(Q = Br, X not = Br or I)

XIV

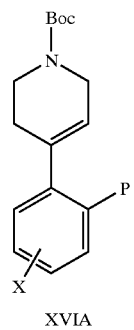

XVIA

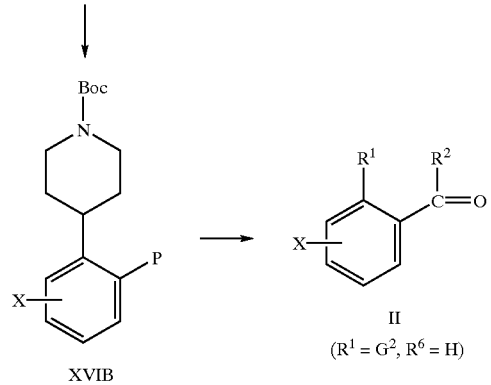

XVIB

II
($R^1 = G^2$, $R^6 = H$)

SCHEME 3

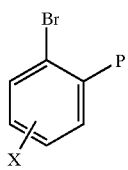

XIV

-continued

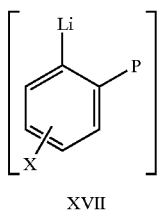

XVII

↓

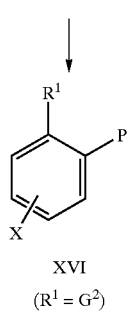

XVI
(R¹ = G²)

Scheme 1 illustrates a method of synthesizing compounds of the formula I wherein the dashed line represents a double carbon-carbon bond and R¹ is a group of the formula G¹, G³, G⁴, G⁵, G⁶ or G⁷. Referring to Scheme 1, a compound of the formula III, wherein Q is a suitable leaving group (e.g., chloro, fluoro, bromo, mesylate, tosylate, etc.), is reacted with a compound of the formula R¹H, wherein H refers to a hydrogen atom on group E or on nitrogen atoms from G¹, G³, G⁵, G⁶ or G⁷ and R¹ is a group of the formula G¹, G³, G⁴, G⁵, G⁶ or G⁷ in the presence of a base, to form the corresponding compound of formula II. This reaction is generally carried out at a temperature from about 0° C. to about 140° C., preferably at about the reflux temperature, in a polar solvent such as dimethyl sulfoxide (DMSO), N,N-dimethylformamide (DMF), N,N-dimethylacetamide (DMA) or N-methyl-2-pyrrolidinone (NMP), preferably DMF. Suitable bases include anhydrous sodium carbonate (Na₂CO₃), potassium carbonate (K₂CO₃), sodium hydroxide (NaOH) and potassium hydroxide (KOH), as well as amines such as pyrrolidine, triethylamine and pyridine. Anhydrous potassium carbonate is preferred.

Compounds of formula II can be converted into compounds of the formula I, wherein R¹ is other than hydrogen, by subjecting them to an aldol condensation or Wittig reaction. For example, in the case of an aldol condensation, a compound of the formula II can be reacted with a compound of the formula

IV

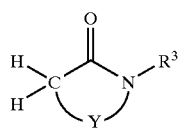

in the presence of a base, to form an aldol intermediate of the formula

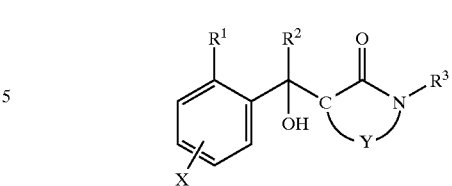

V which may be isolated or converted directly in the same reaction step to a compound of the formula I by the loss of water. The degree of completion for the conversion of compounds of the formula II to the aldol product of formula I may be assessed using one or more analytical techniques, such as thin layer chromatography (tlc) or mass spectrometry. In some instances it may be possible or desirable to isolate the intermediate of formula V. In such case, the compound of formula V may be converted into the compound of formula I by the elimination of water using techniques which are familiar to those skilled in the art, for example, by heating to the reflux temperature a solution of the compound of formula V in a solvent such as benzene, toluene or xylene, in the presence of a catalytic amount of benzene- or p-toluene-sulfonic acid with provision for the removal of the water generated. Such water removal techniques may involve the use of molecular sieves or a Dean-Stark trap to isolate the water created as an azeotrope with the solvent.

The aldol reaction is typically carried out in a polar solvent such as DMSO, DMF, tetrahydrofuran (THF), methanol or ethanol, at a temperature from about −78° C. to about 80° C. Preferably, this reaction is carried out in THF at about 25° C. Suitable bases for use in the aldol formation step include potassium carbonate (K₂CO₃), sodium carbonate (Na₂CO₃), sodium hydride (NaH), sodium methoxide, sodium methoxide, potassium-tert.-butoxide, lithium diisopropylamide, pyrrolidine and piperidine. Sodium hydride is preferred. Aldol condensations are described in "Modern Synthetic Reactions," Herbert O. House, 2d. Edition, W. A. Benjamin, Menlo Park, Calif., 629–682 (1972) and *Tetrahedron*, 38 (20), 3059 (1982).

Compounds of the formula I, wherein R³ is other than hydrogen, can also be prepared from compounds of formula II by reaction with a compound of the formula IV, wherein R³ is hydrogen or —(C=O)R¹³, wherein R¹³ is (C₁–C₆) alkyl or trifluoromethyl, followed by removal of the —C(=O)R¹³ group, if present, and reaction with a compound of the formula R³—L' wherein L' is a leaving group and is defined as Q is defined as above. These reactions can be carried out in a solvent such as di-(alkyl)ether, THF, DMF, DMA or DMSO, preferably DMF, in the presence of a base such as potassium carbonate, sodium carbonate, sodium hydride, potassium hydride, sodium hydroxide or potassium hydroxide, preferably sodium hydride. Reaction temperatures can range from about 0° C. to about 150° C., preferably from about 25° C. to about the reflux temperature of the solvent.

Alternatively, the compound of formula IV can be converted into a compound of the formula I by means of a Wittig olefination, as described in *Helvetica Chimica Acta*, 46, 1580 (1963), and depicted below.

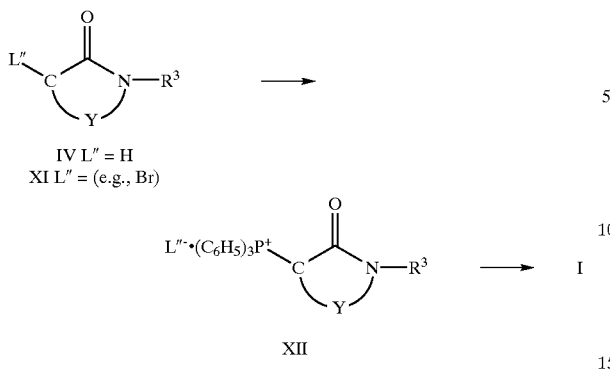

IV L″ = H
XI L″ = (e.g., Br)

I

XII

Thus, the compound of formula IV can be converted into the corresponding bromide of formula XI using standard bromination conditions, followed by treatment with triphenylphosphine in anhydrous THF to form the intermediate of formula XII. The compound of formula XII can then be treated with a base (e.g., aqueous $Na_2CO_3$) to generate the corresponding phosphonium ylide, which can then be reacted with the appropriate intermediate of formula II to produce compounds of general formula I. This transformation is described in A. Maercker, *Organic Reactions*, 14, 270 (1965).

Compounds of the formula I wherein the dashed line represents a single carbon-carbon bond may be prepared by hydrogenating the corresponding compounds wherein the dashed line represents a double carbon-carbon bond, using standard techniques that are well known to those skilled in the art. For example, reduction of the double bond may be effected with hydrogen gas ($H_2$), using catalysts such as palladium on carbon (Pd/C), palladium on barium sulfate (Pd/$BaSO_4$), platinum on carbon (Pt/C), or tris (triphenylphosphine) rhodium chloride (Wilkinson's catalyst), in an appropriate solvent such as methanol, ethanol, THF, dioxane or ethyl acetate, at a pressure from about 1 to about 5 atmospheres and a temperature from about 10° C. to about 60° C., as described in *Catalytic Hydrogenation in Organic Synthesis*, Paul Rylander, Academic Press Inc., San Diego, 31–63 (1979). The following conditions are preferred: Pd on carbon, methanol at 25° C. and 50 psi of hydrogen gas pressure. This method also provides for introduction of hydrogen isotopes (ie. deuterium, tritium) by replacing $^1H_2$ with $^2H_2$ or $^3H_2$ in the above procedure.

An alternative procedure employing the use of reagents such as ammonium formate and Pd/C in methanol at the reflux temperature under an inert atmosphere (e.g., nitrogen or argon gas) is also effective in reducing the carbon-carbon double bond of compounds of the formula I. Another alternative method involves selective reduction of the carbon-carbon bond. This can be accomplished using samarium and iodine or samarium iodide ($SmI_2$) in methanol or ethanol at about room temperature, as described by R. Yanada et. al., *Synlett.*, 443–4 (1995).

The starting materials of the formulas III and IV are either commercially available or known in the art. For example, compounds of formula III in which $R^2$ is hydrogen are readily available from commercial sources or may be prepared using procedures disclosed in the chemical literature. Compounds of the formula III may also be prepared from the corresponding carboxylic acids or esters, (e.g., formula III) wherein $R^2$=OH or O-alkyl), which are commercially available. These acids or esters can be reduced to the corresponding alcohols of formula XIII, depicted below, wherein Q is defined as for formula III, using one or more of a variety of reducing agents and conditions, depending upon the nature of the substituents Q and X.

XIII

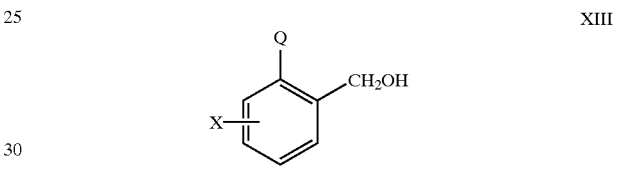

Such reducing agents include sodium borohydride ($NaBH_4$), sodium cyanoborohydride ($NaCNBH_3$), lithium aluminum hydride ($LiAlH_4$) and borane in THF ($BH_3$.THF) in solvents such as methanol, ethanol, THF, diethyl ether and dioxane. Oxidation of the alcohol of formula XIII to the corresponding aldehyde of formula II may be accomplished using a selective oxidizing agent such as Jones reagent (hydrogen chromate ($H_2CrO_4$)), pyridinium chlorochromate (PCC) or manganese dioxide ($MnO_2$). References for such conversions are readily available (a., K. B. Wiberg, *Oxidation in Organic Chemistry. Part A*, Academic Press Inc, N.Y., 69–72 (1965)).

Compounds of the formula IV are also commercially available or can be made by methods well know to those of ordinary skill in the art. Examples of sources of the various compounds of formula IV are presented in Tables 1–3.

TABLE 1

5 MEMBERED HETEROCYCLES

IV

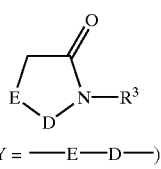

(Y = ―E―D―)

| Name | D | E | Reference |
|---|---|---|---|
| 1,3-oxazolidin-4-one | $CH_2$ | O | DE 2,339,185; Synthesis, 5, 426–428 (1982); U.S. Pat. No. 2,762,815; Arzneim, Forsch., 27, 766–770 (1977). |
| 1,3-oxazolidin-2,4-dione | C=O | O | Parravicini et al., Farmaco Ed. Sci., 31, 49–57 (1976); Kricheldorf, Makromol. Chem., 176, 57–74 (1975). |

TABLE 1-continued

5 MEMBERED HETEROCYCLES

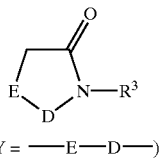

IV (Y = —E—D—)

| Name | D | E | Reference |
|---|---|---|---|
| 4,5-dihydro-1,2-oxazolidin-3-one | O | $CH_2$ | J. Korean Chem. Soc., 36 (3), 453–459 (1992). |
| 1,3-thiazolidin-4-one | $CH_2$ | S | EP 626,377; Hansen, Tet. Lett., 35, (38), 6971–6974 (1994). |
| 1,3-thiazolidin-2,4-dione | C=O | S | Markley, J.A.C.S., 52, 2137–2140 (1930); Dains, J.A.C.S., 43, 615 (1921); Barbry et al., J. chem. Soc. Perkin Trans, 2. (1), 133–140 (1990); Hansen et al., Tetrahedron Lett., 35, (38), 6971–6974 (1994). |
| 1,3-imidazolidin-4-one | $CH_2$ | NH | Fitzi, Angew. Chem. Int. Ed. Eng., 25, 345 (1986); J. Het. Chem., 18 (5), 963 (1981); Heterocycles, 20 (8), 1615 (1983). |
| 1,3-imidazolidin-2,4-dione | C=O | NH | Ware, Chem. Rev., 46, 403–470 (1950); Freter et al., Justus Liebigs Ann. Chem., 607, 174–184 (1957). |
| 1,2-pyrazolidin-3-one | NH | $CH_2$ | Japanese Pat. 1,056,161; J.O.C., 40, 3510 (1975); Org. Synth., 48, 8 (1968). |
| 1,2-thiazolidin-1,1,3-trione | $SO_2$ | $CH_2$ | Rasmussen, et al., Chem. Reviews, 76, 389 (1976). |
| 1,2-thiazolidin-3-one | S | $CH_2$ | Luettringhaus et al., Justus Liebigs Annal. Chem., 679, 123–135 (1964); Ibid, Angew. Chem., 76, 51 (1964). |

TABLE 2

6 MEMBERED HETEROCYCLES

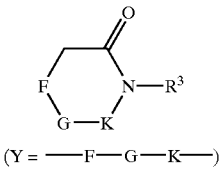

IV (Y = —F—G—K—)

| Name | F | G | K | Reference |
|---|---|---|---|---|
| tetrahydro-1,2-oxazin-3-one | $CH_2$ | $CH_2$ | O | Khomutov et al., Bull. Acad. Sci. USSR Div. Chem. Sci., 1006–1008 (1962); Nally et al., Tet. Lett., 26, 4107, (1985). |
| tetrahydro-1,3-oxazin-4-one | $CH_2$ | O | $CH_2$ | Kalyuskii et al., J. Org. Chem., 25, (10), 1989–1991 (1989); Linde et al., Arzneim, Forsch., 28, 937–939 (1978). |
| tetrahydro-1,3-oxazin-2,4-dione | $CH_2$ | O | C=O | Back et al., Tet. Lett., 2651–4 (1977). |
| morpholin-3-one | O | $CH_2$ | $CH_2$ | U.S. Pat. No. 3,092,630; Australian Patent 9,063,019; Tulyaganov et al., J.O.C. U.S.S.R., (Eng Tran) 6, 1311–1314 (1970); J.A.C.S., 58, 2338 (1936). |
| morpholin-3,5-dione | O | $CH_2$ | C=O | Hadley, et al., Tet. Lett, 24 (1), 91 (1983). |
| 2,3-dihydro-1,4-oxazin-3-one | O | CH* | CH* | Vliet et al., Tetrahedron, 41 (10), 2007–2014 (1985). |
| tetrahydro-1,3-thiazin-4-one | $CH_2$ | S | $CH_2$ | Krus et al., Zh. Org. Khim., 24 (8), 1576, (1988); Bergmann et al., Recl. Trav. Chim. Pays-Bas., 78, 327–330 (1959); Nagakura et al., Heterocycles, 3, 453 (1975). |
| tetrahydro-1,3-thiazin-2,4-dione | $CH_2$ | S | C=O | Hendry et al., JACS, 80, 973 (1958); Sohda et al., Chem. Pharm. Bull., 30, 3563 (1982); U.S. Pat. No. 4,352,929. |
| tetrahydro-1,2-thiazin-3-one | $CH_2$ | $CH_2$ | S | Kharasch, J.O.C., 28, 1901–1902 (1963). |
| thiomorpholin-3-one | S | $CH_2$ | $CH_2$ | Davies, J. Chem. Soc., 117, 298–306 (1920). |
| thiomorpholin-3,5-dione | S | $CH_2$ | C=O | Schulze, Zeitschrift Fur Chem., 182 (1866); Wolfe et al., J.O.C., 35, 3600–7 (1970). |
| 2,3-dihydro-1,4-thiazin-3-one | S | CH* | CH* | Hojo et al., Synthesis, 272 (1979); Masuda et al., Tet. Lett., 32 (6) 1195 (1991). |
| hexahydro-1,2-diazin-3-one | $CH_2$ | $CH_2$ | NH | Hwang et al., Heterocycles, 36 (2), 219 (1993); Taylor et al., J.O.C., 52, 4107 (1987). |
| 4,5-dihydro-2H-pyridazin-3-one | $CH_2$ | CH* | N* | Reichett et al., Synthesis, 9, 786–787 (1984); Amorosa, Ann. Chim. (Rome), 49, 322–329 (1959). |
| hexahydro-1,3-diazin-4-one | $CH_2$ | NH | $CH_2$ | Yamamoto et al., Synthesis, 6, 686, 1985; Skaric et al., Croat. Chem. Acta., 38, 1–4 (1966). |
| hexahydro-1,3-diazin-2,4-dione | $CH_2$ | NH | C=O | Yamamoto et al., Synthesis, 6, 686, 1985; Zee-Cheng et al., J. Org. Chem., 26, 1877 (1961); Beckwith et al., J. Chem. Soc., C, 2756 (1968). |

TABLE 2-continued

6 MEMBERED HETEROCYCLES

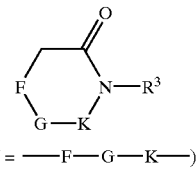

(Y = —F—G—K—)

IV

| Name | F | G | K | Reference |
|---|---|---|---|---|
| piperazin-2-one | NH | CH$_2$ | CH$_2$ | E.P. 264,261; J.A.C.S., 51, 3074 (1929); Rees, J. Het. Chem., 24, 1297 (1987); U.S. Pat. No. 3,037,023. |
| piperazin-2,6-dione | NH | CH$_2$ | C═O | J.A.C.S., 51, 3074 (1929); U.S. Pat. No. 3,037,023. |
| tetrahydro-1,3,4-thiadiazin-5-one | S | CH$_2$ | NH | Japanese Pat. 3,083,972 (1991); Matsubara et al., Chem. Pharm. Bull., 32 (4), 1590 (1984). |
| 5,6-dihydro-1,3,4-thiadiazin-5-one | S | CH* | N* | Matsubara et al., Chem. Pharm. Bull., 32 (4) 1590 (1984). |
| 1,3,4-oxadiazin-5-one | O | CH$_2$ | NH | Bennouna, et al., J. Hetero. Chem, 16, 161 (1979). |
| 5,6-dihydro-1,2,4-oxadiazin-5-one | O | N* | CH* | Japanese Pat. 3,148,267. |
| tetrahydro-1,2,4-oxadiazin-5-one | O | NH | CH$_2$ | Japanese Pat. 3,148,267. |
| 1,2,4-triazin-5-one | NH | NH | CH$_2$ | Anderson et al., Tet., 39, 3419 (1983); Schulz et al., Chem. Ber., 122, 1983 (1989). |
| tetrahydro-1,2,4-oxadiazin-5-one | O | NH | CH$_2$ | Hussein, Hetercycles, 26, 163 (1987). |
| 5,6-dihydro-1,2,4-oxadiazin-5-one | O | N* | CH* | Hussein, Hetercycles, 26, 163 (1987). |
| 1,2,4-oxadiazin-3,5-dione | O | NH | C═O | Rajagopalan et al., J.C.S. Chem. Commun., 167 (1970). |
| 1,2,4-triazin-6-one | NH | CH$_2$ | NH | Anderson et al., Tetrahedron, 39 (20), 3419 (1983); Schulz et al., Chem. Ber., 122, 1983 (1989). |

*Ring atom is sp$^2$ hybridized.

TABLE 3

7 MEMBERED HETEROCYCLES

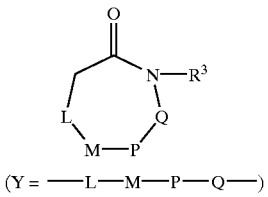

(Y = —L—M—P—Q—)

IV

| Name | L | M | P | Q | Reference |
|---|---|---|---|---|---|
| hexahydro-1,2-oxazepin-3-one | CH$_2$ | CH$_2$ | CH$_2$ | O | Amiaiky et al., Synthesis, 5, 426–428, (1982). |
| hexahydro-1,3-oxazepin-4-one | CH$_2$ | CH$_2$ | O | CH$_2$ | Bergmann et al., Recl. Trav. Chim. Pays-Bas., 78, 327–330 (1959). |
| hexahydro-1,4-oxazepin-3-one | O | CH$_2$ | CH$_2$ | CH$_2$ | Brown et al., J. Chem. Soc., Perkin Trans., 1, 557 (1987); Farberow et al., Zh. Obshch. Khim., 25, 133–135 (1955); Grouiller et al., J. Heterocycl. Chem., 13, 853–859 (1976). |
| hexahydro-1,4-oxazepin-3,5-dione | O | CH$_2$ | CH$_2$ | C═O | See "Detailed Description". |
| 2,3,5,6-tetrahydro-1,4-oxazepin-5,7-dione | C═O | O | CH$_2$ | CH$_2$ | Brown et al., Synth. Commun., 18, 1801 (1988). |
| hexahydro-1,4-oxazepin-5-one | CH$_2$ | O | CH$_2$ | CH$_2$ | Farberow et al., Zh. Obshch. Khim., 25, 133–135 (1955); Kato et al., Chem. Ph. Bull., 17 (12), 2405–2410 (1969). |
| hexahydro-1,3-oxazepin-2,4-dione | CH$_2$ | CH$_2$ | O | C═O | See "Detailed Description". |
| hexahydro-1,2-thiazepin-3-one | CH$_2$ | CH$_2$ | CH$_2$ | S | Black, J. Chem. Soc. C, 1708–1710 (1966); Can. J. Chem., 49, 2612–2616 (1971); J. Org. Chem., 46, 7, 1239–1243 (1981); and J. Org. Chem., 25, 1953–1956 (1960); DE 1,195,317. |
| hexahydro-1,4-thiazepin-3-one | S | CH$_2$ | CH$_2$ | CH$_2$ | Hill et al., JACS, 95 (9), 2923–2927 (1973). |
| 2,3,4,5-tetrahydro-1,4-thiazepin-3-one | S | CH* | CH* | CH$_2$ | Defoin et al., Helv. Chim. Acta., 68, 1998 (1985). |
| hexahydro-1,4-thiazepin-3,5-dione | S | CH$_2$ | CH$_2$ | C═O | See "Detailed Description". |
| hexahydro-1,4-thiazepin-3,5-dione | CH$_2$ | S | CH$_2$ | C═O | See "Detailed Description". |
| 2,3,6,7-tetrahydro-1,4-thiazepin-5-one | CH$_2$ | S | CH$_2$ | CH$_2$ | Jakob et al., Ber. Deutsch Chem. Ges., 96, 88 (1963). |
| 6,7-dihydro-1,4-thiazepin-5-one | CH$_2$ | S | CH* | CH* | Yamamoto et al., Ang. Chem. Int. Ed. Engl., 25 (7), 635 (1986). |

TABLE 3-continued

7 MEMBERED HETEROCYCLES

IV

![structure with ketone, N-R³, L, M, P, Q in 7-membered ring]

(Y = —L—M—P—Q—)

| Name | L | M | P | Q | Reference |
|---|---|---|---|---|---|
| hexahydro-1,3-thiazepin-2,4-dione | $CH_2$ | $CH_2$ | S | C=O | Hanefield et al., Liebigs Ann, Chem., 4, 337–344 (1992). |
| hexahydro-1,2-diazepin-3-one | $CH_2$ | $CH_2$ | $CH_2$ | N | Rutjes et al., Tetrahedron Lett., 32, 45, 6629–6632 (1991); and Fritschi et al., Helv. Chem. Acta., 74, 8, 2024–2034 (1991). |
| hexahydro-1,3-diazepin-2,4-dione | $CH_2$ | $CH_2$ | NH | C=O | Breckenridge, J. Chem. Res., Miniprint, 6, 166 (1982); Gunawardane, Indian J. Chem. Sect. A, 27, 5, 380–386 (1988). |
| hexahydro-1,4-diazepin-2-one | NH | $CH_2$ | $CH_2$ | $CH_2$ | U.S. Pat. No. 4,814,443; Poppelsdorf et al., J. Org. Chem., 26, 131–134 (1961); Ziegler et al., J. Med. Chem., 33, 1, 142–146 (1990). |
| hexahydro-1,4-diazepin-5-one | $CH_2$ | NH | $CH_2$ | $CH_2$ | Crombie et al., J. Chem. Soc. Chem. Commun., 959 (1983); Groves et al., J.A.C.S., 106 (3), 630 (1984). |
| hexahydro-1,4-diazepin-5,7-dione | C=O | N | $CH_2$ | $CH_2$ | Kappe et al., Angew. Chem. Int. Ed. Engl., 13, 491 (1974); Bonsignore et al., Heterocycles, 26 (6), 1619 (1987). |
| hexahydro-1,3,5-thiadiazepin-2,6-dione | S | C=O | NH | $CH_2$ | Vass, Synthesis, 10, 817 (1986). |
| 4,5,6,7-tetrahydro-1,3,5-thiadiazepin-6-one | S | CH* | N* | $CH_2$ | Vass et al., Synthesis, 10, 817 (1986). |
| 2,3,5,6-tetrahydro-1,2,4-triazepin-3,5-dione | CH* | N* | NH | C=O | Hasnaoui et al., Rec. Trav. Chim. P.-Bas, 99, 301 (1980). |

*Ring atom is $sp^2$ hybridized.

Compounds of the formula IV, wherein Y is —L—M—P—Q, and L is sulfur or oxygen, M and P are —$CH_2$— and Q is —(C=O)—, can be prepared according to the following procedure. Said compound of the formula IV, depicted below,

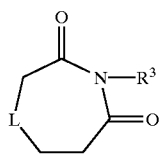

IV (Y=L—M—P—Q, L is sulfur or oxygen, M=P=—$CH_2$—, Q=—(C=O)—)

wherein L is sulfur or oxygen, is prepared by reacting an anhydride of the formula

XXXI

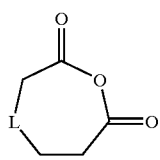

wherein L is sulfur or oxygen, with an amine of the formula $R^3NH_2$ according to the method detailed by Meyers (*JOC*, 54 (17) 4243 (1989)), Fickenscher (*Arch. Pharm.*, 307, 520 (1976)) or Cole et al., (*J. Med. Chem.*, 13, 565 (1970)).

The anhydride of the formula XXXI can be prepared by reacting a diacid of the formula

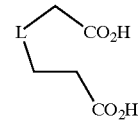

XXX wherein L is sulfur or oxygen, with acetic anhydride, according to the methods described in Vogel's *Textbook of Practical Organic Chemistry*, 499–501 (4th Ed., Longman House, London UK, 1970).

The compound of the formula XXX is commercially available or can be made according to the procedure of Woodward and Eastman, *J.A.C.S.*, 68, 2229 (1946).

Compounds of the formula IV, wherein Y is —L—M—P—Q, and L and M are carbon, P is oxygen and Q is —(C=O)—, can be prepared according to the following procedure. Said compound of the formula IV, depicted below,

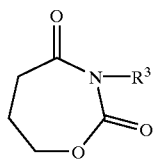

IV (Y=L—M—P—Q, L=M=$CH_2$, P=oxygen, Q=—(C=O)—)

is prepared from a compound of the formula

XXXIV

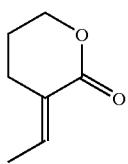

according to the method described by Back et al., *Tet. lett.*, 2651—2654 (1977). The compound of the formula XXXIV can be prepared according to the method of Ksander, et al., *JOC*, 42, (7), 1180–1185 (1977).

Compounds of the formula IV, wherein $R^3$ is hydrogen (compounds of the formula IVA), may be alkylated to form the corresponding compounds wherein $R^3$ is not hydrogen using standard techniques available to those skilled in the art, e.g., by (a) generation of the anion of the desired compound of formula IVA using a strong base/polar solvent system such as NaH/THF, NaH/DMF or n-butyllithium/THF (n-buLi/THF), at a temperature from about −30° C. to about the reflux temperature of the solvent, for a period of about 5 minutes to about 24 hours, and (b) treatment of the anion with an alkylating agent of the formula $R^3L'$ wherein L' is a leaving group such as chloro, bromo, iodo or mesylate. This process is depicted below.

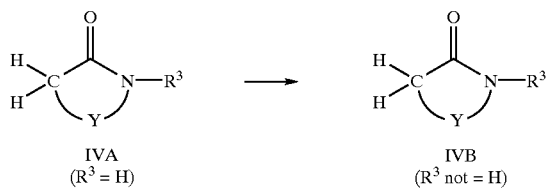

IVA
($R^3$ = H)

IVB
($R^3$ not = H)

The foregoing conversion of compounds of the formula IVA to those of the formula IVB may also be achieved using phase transfer catalysis conditions as described by Takahata et al., *Heterocycles*, 1979, 12(11), pp. 1449–1451.

Compounds of the formula IVB wherein $R^3$ is aryl or heteroaryl can be prepared from compounds of the formula IVA by reaction with an aryl or heteroaryl reagent of the formula $R^3L'$, wherein L' is a leaving group such as chloro, bromo or iodo, in the presence of a catalyst such as copper (0) or copper (I) (such as copper, copper-bronze, or copper bromide) and a base, such as sodium hydride, potassium carbonate, or sodium carbonate. The reaction may be run neat or with a polar solvent such as dimethyl formamide, or dimethyl sulfoxide. This reaction, referred to as an Ullmann condensation, is described by Yamamoto & Kurata, *Chem. and Industry*, 737–738 (1981).

The compounds of formula $R^1H$ used in the preparation of intermediates of the formula II are readily available or may be prepared using standard methods of organic synthesis known to those skilled in the art and adapted from procedures disclosed in the chemical literature. For example, the preparation of compounds of the formula $R^1H$, wherein $R^1$ is $G^1$, may be accomplished using the following reaction sequence, beginning with commercially available N-tert-butoxycarbonyl piperazine (VI):

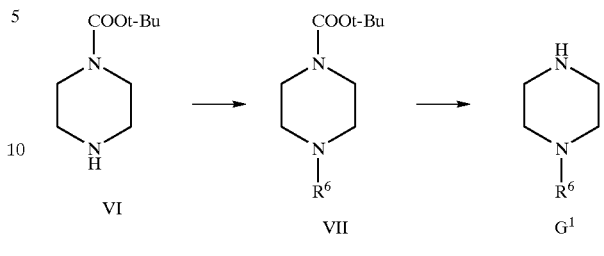

Alkylation of the compound of formula VI with a compound of the formula $R^6L'$ wherein L' is a leaving group, and is defined as Q is defined above and $R^6$ is $(C_1-C_6)$alkyl, aryl-$(C_1-C_4)$alkyl wherein the aryl moiety is phenyl or naphthyl, or heteroaryl—$(CH_2)_q$—, wherein q is zero, one, two, three or four, and the heteroaryl moiety is selected from pyridyl, pymidyl, benzoxazolyl, benzothiazolyl, benzisoxazolyl, and benzisothiazolyl, in the presence of an acid scavenger (e.g., sodium bicarbonate ($NaHCO_3$), potassium bicarbonate ($KHCO_3$), sodium carbonate ($Na_2CO_3$) or potassium carbonate ($K_2CO_3$)), in a polar solvent such as acetone at a temperature of about 10° C. to about the reflux temperature of the solvent, will yield the intermediate of formula VII. Removal of the tert-butoxycarbonyl group can be accomplished using acidic conditions, e.g., HBr in acetic acid or trifluoroacetic acid until the reaction is judged to be complete.

Compounds of the formula II, wherein $R^1$ is tetrahydropyridine or piperidine (i.e. compounds of the formula $G^2$) and $R^2$ is hydrogen, can be prepared from the 2-bromobenzaldehyde of formula III, many of which are commercially available, as depicted in Scheme 2. Referring to Scheme 2, the compound of formula III is first converted into a protected aldehyde of the formula XIV, wherein P represents the entire protected aldehyde or ketone moiety, using methods well known in the art. For example, the 1,3-dioxolane derivative of the aldehyde may be prepared according to the method described by J. E. Cole et al., *J. Chem. Soc.*, 244 (1962), by refluxing a solution of the aldehyde of formula III and 1,3-propanediol in anhydrous benzene with a catalytic amount of p-toluenesulfonic acid. When $R^2$ of formula III is not hydrogen, the ketone can be protected using an appropriate protecting group. Appropriate protecting groups can be chosen from many such groups based on the presence and nature of the substituent X. Examples of suitable protecting groups may be found in T. W. Greene and P. Wuts, *Protecting Groups in Organic Synthesis*, John Wiley & Sons, 2nd Edition, New York, 1991. The most preferred protecting groups are those that are resistant to catalytic hydrogenation (e.g., 1,3-dioxolane), which would therefore allow for the subsequent reduction, if required, of the carbon-carbon double bond of the tetrahydropyridines of formula XVIA.

Compounds of the formula XIV can then be treated with vinylstannanes of the formula

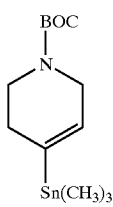

XV for example, 1-BOC-4-trimethylstannyl-1,2,5,6-tetrahydropyridine (wherein BOC refers to tert-butyloxycarbonyl), in the presence of a catalyst, to form the corresponding compound of formula XVIA. Palladium is the preferred catalyst (for example, $((C_6H_5)_3P)_4Pd$ or $Pd_2(dba)_3$), wherein dba refers to dibenzylidene acetone. Suitable solvents for the aforesaid reaction include neat, acetonitrile, dimethylformamide, N-methyl-2-pyrrolidinone, preferably dimethylformamide. This reaction is conveniently run at about 20° C. to about 160° C., preferably about 60° C. to about 130° C. This reaction may be carried out as described in "Palladium-catalyzed Vinylation of Organic Halides" in *Organic Reactions*, 27, 345–390, (W. G. Dauben, Ed., John Wiley & Sons, Inc., New York, N.Y., 1982).

Compounds of the formula XVIA can be converted into compounds of the formula II, wherein $R^1$ is tetrahydropyridine by removal of the aldehyde or ketone protecting group. The protecting group for the aldehyde or ketone, P, can be converted into the unprotected ketone or aldehyde of the formula $-C(=O)R^2$ using one or more of the techniques described in Greene, for example, stirring a solution of the compound of formula XVI in THF and 5% hydrochloric acid at room temperature for 20 hours.

Alternatively, compounds of formula XVIA can be converted into compounds of the formula II, where $R^1$ is piperidine ($G^2$), by catalytic hydrogenation of the tetrahydropyridine of formula XVIA, from the previous paragraph, using standard methods known in the art, generally using palladium on carbon as the catalyst, to form the corresponding compounds of formula XVIB. This reaction is typically performed in an inert solvent, such as ethanol or ethyl acetate, either with or without a protic acid such as acetic acid or hydrochloric acid (HCl). Acetic acid is preferred. The protecting groups on $G^2$ (e.g., BOC) can be removed using one or more of the techniques described in Greene, referred to above, for example, stirring the compound of formula XVI in ethyl acetate and 3 molar hydrochloric acid at about room temperature for about 30 minutes. The protecting group for the aldehyde or ketone, P, can be converted into the unprotected ketone or aldehyde as described above.

Compounds of the formula XIV from reaction Scheme 2 may also be treated with alkyllithium reagents, for example n-butyllithium, sec-butyllithium or tert-butyllithium, preferably n-butyllithium in an inert solvent, as shown in Scheme 3, to form the intermediate lithium anion of formula XVII. Suitable solvents for this reaction include, for example, ether or tetrahydrofuran, preferably tetrahydrofuran. Reaction temperatures can range from about –110° C. to about 0° C. The intermediate lithium anions of formula XVII can then be further reacted with a suitable electrophile, selection of which depends on the presence and nature of the substituent. Suitable electrophiles for use in preparing compounds of the formula II wherein $R^1$ is a group of the formula $G^2$ include, for example, carbonyl derivatives or alkylating agents (e.g., 1-BOC-4-piperidone). In the case where an aldehyde or ketone is used as the electrophile, the hydroxy group must be removed from the intermediate of formula XVIII, as depicted below, in order to form the corresponding compound of formula II.

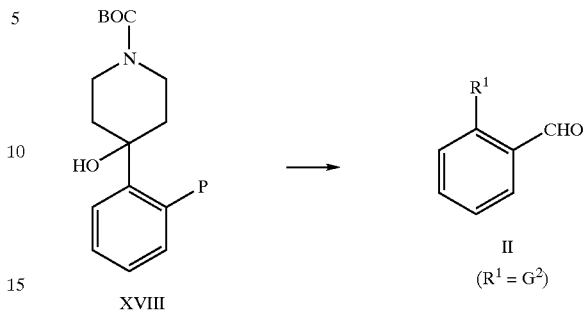

This step may be accomplished by one of several standard methods known in the art. For example, a thiocarbonyl derivative such as a xanthate may be prepared and removed by free radical processes, both of which are known to those skilled in the art. Alternatively, the hydroxyl group may be removed by reduction with a hydride source such as triethysilane under acidic conditions, using, for example, trifluoroacetic acid or boron trifluoride. The reduction reaction can be performed neat or in a solvent such as methylene chloride. A further alternative would be to first convert the hydroxyl group to a suitable leaving group, such as tosylate or chloride, using standard methods known in the art, and then to remove the leaving group with a nucleophilic hydride, such as, for example, lithium aluminum hydride. The latter reaction is typically performed in an inert solvent such as ether or tetrahydrofuran. Also, a reducing agent may be used to reductively remove the benzylic substituent. Suitable reducing agents include, for example, Raney nickel in ethanol and sodium or lithium in liquid ammonia. Another alternative method for removing the hydroxyl group is to first dehydrate the alcohol of formula XVIII to an olefin of the formula XVIA (i.e. see Scheme 2) with a reagent such as Burgess salt (*J. Org. Chem.*, 38, 26 (1973)) and then to catalytically hydrogenate the double bond under standard conditions with a catalyst such as palladium on carbon. The alcohol may also be dehydrated to the olefin by treatment with acids such as p-toluenesulfonic acid.

Compounds of the formula II, wherein $R^1$ is $G^2$ and $R^6$ is hydrogen, can be converted into the corresponding compounds of the formula II, wherein $R^1$ is $G^2$ and $R^6$ is other than hydrogen, by reacting them with a compound of the formula $R^6L'$, as described above in Scheme 1, for preparing compounds of the formula VII.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate. lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^3$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

Compounds of the formula I and their pharmaceutically acceptable salts (hereinafter also referred to, collectively, as "the active compounds") are useful psychotherapeutics and are potent agonists and/or antagonists of the serotonin 1A ($5\text{-}HT_{1A}$) and/or serotonin 1D ($5\text{-}HT_{1D}$) receptors. The active compounds are useful in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive-compulsive disorder, panic disorder, memory disorders (e.g., dementia, amnestic disorders, and age-related cognitive decline (ARCD)), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, Fibromyalgia Syndrome, stress incontinence, Tourette syndrome, trichotillomania, kleptomania, male impotence, cancer (e.g. small cell lung carcinoma), chronic paroxysmal hemicrania and headache (associated with vascular disorders).

The affinities of the compounds of this invention for the various serotonin-1 receptors can be determined using standard radioligand binding assays as described in the literature. The $5\text{-}HT_{1A}$ affinity can be measured using the procedure of Hoyer et al. (*Brain Res.*, 376, 85 (1986)). The $5\text{-}HT_{1D}$ affinity can be measured using the procedure of Heuring and Peroutka (*J. Neurosci.*, 7, 894 (1987)).

The in vitro activity of the compounds of the present invention at the $5\text{-}HT_{1D}$ binding site may be determined according to the following procedure. Bovine caudate tissue is homogenized and suspended in 20 volumes of a buffer containing 50 mM TRIS.hydrochloride (tris [hydroxymethyl]aminomethane hydrochloride) at a pH of 7.7. The homogenate is then centrifuged at 45,000 G for 10 minutes. The supernatant is then discarded and the resulting pellet resuspended in approximately 20 volumes of 50 mM TRIS.hydrochloride buffer at pH 7.7. This suspension is then pre-incubated for 15 minutes at 37° C., after which the suspension is centrifuged again at 45,000 G for 10 minutes and the supematant discarded. The resulting pellet (approximately 1 gram) is resuspended in 150 ml of a buffer of 15 mM TRIS.hydrochloride containing 0.01 percent ascorbic acid with a final pH of 7.7 and also containing 10 $\mu$M pargyline and 4 mM calcium chloride ($CaCl_2$). The suspension is kept on ice at least 30 minutes prior to use.

The inhibitor, control or vehicle is then incubated according to the following procedure. To 50 $\mu$l of a 20 percent dimethylsulfoxide (DMSO)/80 percent distilled water solution is added 200 $\mu$l of tritiated 5-hydroxytryptamine (2 nM) in a buffer of 50 mM TRIS.hydrochloride containing 0.01 percent ascorbic acid at pH 7.7 and also containing 10 $\mu$M pargyline and 4 $\mu$M calcium chloride, plus 100 nM of 8-hydroxy-DPAT (dipropylaminotetraline) and 100 nM of mesulergine. To this mixture is added 750 $\mu$l of bovine caudate tissue, and the resulting suspension is vortexed to ensure a homogenous suspension. The suspension is then incubated in a shaking water bath for 30 minutes at 25° C. After incubation is complete, the suspension is filtered using glass fiber filters (e.g., Whatman GF/B-filters™). The pellet is then washed three times with 4 ml of a buffer of 50 mM TRIS.hydrochlonde at pH 7.7. The pellet is then placed in a scintillation vial with 5 ml of scintillation fluid (aquasol 2 ™) and allowed to sit overnight. The percent inhibition can be calculated for each dose of the compound. An $IC_{50}$ value can then be calculated from the percent inhibition values.

The activity of the compounds of the present invention for $5\text{-}HT_{1A}$ binding ability can be determined according to the following procedure. Rat brain cortex tissue is homogenized and divided into samples of 1 gram lots and diluted with 10 volumes of 0.32 M sucrose solution. The suspension is then centrifuged at 900 G for 10 minutes and the supemate separated and recentrifuged at 70,000 G for 15 minutes. The supemate is discarded and the pellet re-suspended in 10 volumes of 15 mM TRIS.hydrochloride at pH 7.5. The suspension is allowed to incubate for 15 minutes at 37° C. After pre-incubation is complete, the suspension is centrifuged at 70,000 G for 15 minutes and the supernate discarded. The resulting tissue pellet is resuspended in a buffer of 50 mM TRIS.hydrochloride at pH 7.7 containing 4 mM of calcium chloride and 0.01 percent ascorbic acid. The tissue is stored at −70° C. until ready for an experiment. The tissue can be thawed immediately prior to use, diluted with 10 $\mu$m pargyline and kept on ice.

The tissue is then incubated according to the following procedure. Fifty microliters of control, inhibitor, or vehicle (1 percent DMSO final concentration) is prepared at various dosages. To this solution is added 200 $\mu$l of tritiated DPAT at a concentration of 1.5 nM in a buffer of 50 mM TRIS.hydrochloride at pH 7.7 containing 4 mM calcium chloride, 0.01 percent ascorbic acid and pargyline. To this solution is then added 750 μl of tissue and the resulting suspension is vortexed to ensure homogeneity. The suspension is then incubated in a shaking water bath for 30 minutes at 37° C. The solution is then filtered, washed twice with 4 ml of 10 mM TRIS.hydrochloride at pH 7.5 containing 154 mM of sodium chloride. The percent inhibition is calculated for each dose of the compound, control or vehicle. $IC_{50}$ values are calculated from the percent inhibition values.

The compounds of formula I of the present invention described in the following Examples were assayed for $5\text{-HT}_{1A}$ and $5\text{-HT}_{1D}$ affinity using the aforementioned procedures. All such compounds of the invention that were tested exhibited $IC_{50}$'s less than 0.60 μM for $5\text{-HT}_{1D}$ affinity and $IC_{50}$'s less than 1.0 μM for $5\text{-HT}_{1A}$ affinity.

The agonist and antagonist activities of the compounds of the invention at $5\text{-HT}_{1A}$ and $5\text{-HT}_{1D}$ receptors can be determined using a single saturating concentration according to the following procedure. Male Hartley guinea pigs are decapitated and $5\text{-HT}_{1D}$ receptors are dissected out of the hippocampus, while $5\text{-HT}_{1D}$ receptors are obtained by slicing at 350 mM on a McIlwain tissue chopper and dissecting out the substantia nigra from the appropriate slices. The individual tissues are homogenized in 5 mM HEPES buffer containing 1 mM EGTA (pH 7.5) using a hand-held glass-Teflon® homogenizer and centrifuged at 35,000×g for 10 minutes at 4° C. The pellets are resuspended in 100 mM HEPES buffer containing 1 mM EGTA (pH 7.5) to a final protein concentration of 20 mg (hippocampus) or 5 mg (substantia nigra) of protein per tube. The following agents are added so that the reaction mix in each tube contained 2.0 mM $MgCl_2$, 0.5 mM ATP, 1.0 mM cAMP, 0.5 mM IBMX, 10 mM phosphocreatine, 0.31 mg/mL creatine phosphokinase, 100 μM GTP and 0.5–1 microcuries of [$^{32}$P]-ATP (30 Ci/mmol: NEG-003—New England Nuclear). Incubation is initiated by the addition of tissue to siliconized microfuge tubes (in triplicate) at 30° C. for 15 minutes. Each tube receives 20 μL tissue, 10 μL drug or buffer (at 10×final concentration), 10 μL 32 nM agonist or buffer (at 10×final concentration), 20 μL forskolin (3 μM final concentration) and 40 μL of the preceding reaction mix. Incubation is terminated by the addition of 100 μL 2% SDS, 1.3 mM CAMP, 45 mM ATP solution containing 40,000 dpm [$^{3}$H]-cAMP (30 Ci/mmol: NET-275—New England Nuclear) to monitor the recovery of cAMP from the columns. The separation of [$^{32}$P]-ATP and [$^{32}$P]-cAMP is accomplished using the method of Salomon et al., *Analytical Biochemistry*, 1974, 58, 541–548. Radioactivity is quantified by liquid scintillation counting. Maximal inhibition is defined by 10 μM (R)-8-OH-DPAT for $5\text{-HT}_{1A}$ receptors, and 320 nM 5-HT for $5\text{-HT}_{1D}$ receptors. Percent inhibitions by the test compounds are then calculated in relation to the inhibitory effect of (R)-8-OH-DPAT for $5\text{-HT}_{1A}$ receptors or 5-HT for $5\text{-HT}_{1D}$ receptors. The reversal of agonist induced inhibition of forskolin-stimulated adenylate cyclase activity is calculated in relation to the 32 nM agonist effect.

The compounds of the invention can be tested for in vivo activity for antagonism of $5\text{-HT}_{1D}$ agonist-induced hypothermia in guinea pigs according to the following procedure.

Male Hartley guinea pigs from Charles River, weighing 250–275 grams on arrival and 300–600 grams at testing, serve as subjects in the experiment. The guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneously (s.c.) prior to a $5\text{-HT}_{1D}$ agonist, such as [3-(1-methylpyrrolidin-2-ylmethyl)-1H-indol-5-yl]-(3-nitropyridin-3-yl)-amine, which can be prepared as described in PCT publication WO93/111 06, published Jun. 10, 1993 which is administered at a dose of 5.6 mg/kg, s.c. Before a first temperature reading is taken, each guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional −30 minute reading is taken. The $5\text{-HT}_{1D}$ agonist is then administered at 0 minutes and temperatures are taken 30, 60, 120 and 240 minutes later.

In subcutaneous screening experiments, a prerug baseline temperature reading is made at −30 minutes. The test compound and $5\text{-HT}_{1D}$ agonists are given concurrently and temperatures are taken at 30, 60, 120 and 240 minutes later.

Data are analyzed with two-way analysis of variants with repeated measures in Newman-Keuls post hoc analysis.

The active compounds of the invention can be evaluated as anti-migraine agents by testing the extent to which they mimic sumatriptan in contracting the dog isolated saphenous vein strip (P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83 (1989).

The serotonin $5\text{-HT}_{1}$ agonist activity can be determined by the in vitro receptor binding assays, as described for the $5\text{-HT}_{1A}$ receptor using rat cortex as the receptor source and [$^{3}$H]-8-OH-DPAT as the radioligand [D. Hoyer et al. *Eur. J. Pharm.*, 118, 13 (1985)] and as described for the $5\text{-HT}_{1D}$ receptor using bovine caudate as the receptor source and [$^{3}$H]serotonin as the radioligand [R. E. Heuring and S. J. Peroutka, *J. Neuroscience*, 7, 894 (1987)]. Of the active compounds tested, all exhibited an $IC_{50}$ in either assay of 1 μM or less.

The compounds of formula I may advantageously be used in conjunction with one or more other therapeutic agents, for instance, different antidepressant agents such as tricyclic antidepressants (e.g., amitriptyline, dothiepin, doxepin, trimipramine, butripyline, clomipramine, desipramine, imipramine, iprindole, lofepramine, nortriptyline or protriptyline), monoamine oxidase inhibitors (e.g., isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor e.a, benserazide or carbidopa, orwith a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

Compounds of the formula I and the pharmaceutically acceptable salts thereof, in combination with a 5-HT re-uptake inhibitor (e.g., fluvoxamine, sertraline, fluoxetine or paroxetine), preferably sertraline, or a pharmaceutically acceptable salt or polymorph thereof (the combination of a compound of formula I with a 5-HT re-uptake inhibitor is referred herein to as "the active combination"), are useful psychotherapeutics and may be used in the treatment or prevention of disorders the treatment or prevention of which is facilitated by enhanced serotonergic neurotransmission (e.g., hypertension, depression, generalized anxiety disorder, phobias, posttraumatic stress syndrome, avoidant personality disorder, sexual dysfunction, eating disorders, obesity, chemical dependencies, cluster headache, migraine pain, Alzheimer's disease, obsessive-compulsive disorder, panic disorder, memory disorders (e.g., dementia, amnestic disorders, and age-associated memory impairment), Parkinson's diseases, dementia in Parkinson's disease, neuroleptic-induced Parkinsonism and tardive dyskinesias), endocrine disorders (e.g., hyperprolactinaemia), vasospasm (particularly in the cerebral vasculature), cerebellar ataxia, gastrointestinal tract disorders (involving changes in motility and secretion) chronic paroxysmal hemicrania and headache (associated with vascular disorders).

Serotonin (5-HT) re-uptake inhibitors, preferably sertraline, exhibit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

U.S. Pat. No. 4,536,518 describes the synthesis, pharmaceutical composition and use of sertraline for depression and is hereby incorporated by reference in its entirety.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifylng agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., depression) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 μg to 1000 μg of the compound of the invention. The overall daily dose with an aerosol will be within the range 100 μg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hard candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg to about 2000 mg, preferably from about 0.1 mg to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg to about 2000 mg, preferably from about 1 mg to about 200 mg of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 µg to about 100 mg of the active compound of this invention, preferably from about 1 µg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of a 5-HT re-uptake inhibitor, preferably sertraline, preferably from about 1 mg to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg to about 100 mg per kg of body weight per day of a 5-HT re-uptake inhibitor, preferably sertraline, preferably from about 0.1 mg. to about 10 mg per kg of body weight per day of sertraline; with from about 0.001 mg. to about 100 mg per kg of body weight per day of a compound of formula I, preferably from about 0.01 mg to about 10 mg per kg of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million (δ) and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 µm silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure means that a rotary evaporator was used.

EXAMPLE 1

3-(4-Chlorobenzyl)-5-[2-(4-methyltiperazin-1-yl)-benzylidene]midazolidine-2,4-dione Under a nitrogen atmosphere in a flame-dried flask, sodium hydride (43 mg, 1.07 mmol, 60% oil dispersion) was washed with hexanes and then treated with tetrahydrofuran (THF) (8 mL), followed by 3-(4-chlorobenzyl)-imidazolidine-2,4-dione (235 mg, 1.04 mmol) and 2-(4-methylpiperazin-1-yl)-benzaldehyde (209 mg, 1.02 mmol), and an additional 2 mL of THF. After refluxing the mixture overnight, the solvent was removed and the residue was treated with aqueous ammonium chloride and aqueous sodium bicarbonate to a pH of 8, then extracted with methylene chloride. The organic extracts were washed with aqueous sodium chloride, dried and concentrated in vacuo to a yellow foam. The foam was crystallized from hot ethyl acetate: hexanes to give a solid, 240 mg (57%).

M.p. 185–187° C. Mass spectrum: 411 ($M^{+1}$). $^1$H-NMR (CDCl$_3$) δ 9.45 (1H, s), 7.37–7.24 (4H, m), 7.16–7.09 (2H, m), 6.72 (1H, s), 4.72 (2H, s), 3.02 (4H, br s), 2.34 (3H, 2). Elemental analysis calculated for $C_{22}H_{23}N_4O_2Cl.0.5\ H_2O$: C, 62.93, H, 5.76, N, 13.34. Found: C, 63.33, H, 5.58, N, 13.58.

The following examples were prepared by an analogous procedure to that of Example 1, except where indicated.

EXAMPLE 2

3-(4-Chlorophenyl)-5-[2-(4-methylpiperazin-1-yl)-benzylidene]-imidazolidine-2,4-dione M.p. 193–193.5° C. Mass spectrum 397 ($M^{+1}$). Elemental analysis calculated for $C_{21}H_{21}N_4O_2Cl.0.5\ CH_3CN$: C, 63.31, H, 5.43, N 15.10. Found: C, 62.93, H, 5.50, N, 15.10.

EXAMPLE 3

3-(4-Chlorobenzyl)-5-[2-(4-methylpiperazin-1-yl)-benzylidene]-thiazolidine-2,4-dione Hydrochloride Hydrate M.p. 240–242° C. Mass spectrum 428 ($M^{+1}$). Elemental analysis calculated for $C_{22}H_{22}N_3O_2SCl.HCl.0.25\ H_2O$: C, 56.35, H, 5.05, N, 8.96. Found: C, 56.18, H, 5.03, N, 8.70.

EXAMPLE 4

4-Benzyl-2-[2-(4-methylpiperazin-1-yl)-benzylidene]-thiomorpholin-3-one

M.p. 106–108° C. Mass spectrum 394 ($M^{+1}$). Elemental analysis calculated for $C_{23}H_{27}N_3OS$: C, 70.20, H, 6.91. N, 10.68. Found: C, 70.19, H, 6.99, N, 10.72. $^1$H-NMR ($CDCl_3$) δ 8.10 (1H, s), 7.64 (1H, dd), 7.53–7.26 (6H, m), 7.08–6.97 (2H, m), 4.80 (2H, s), 3.69 (2H, sym m), 3.01 (4H, t), 2.88 (2H, sym m), 2.63 (4H, br s), 2.38 (3H, s).

EXAMPLE 5

4-(3,4-Dichlorobenzyl)-2-[2-(4-methylpiperazin-1-yl)-benzylidene]-thiomorpholin-3-one Hydrochloride Dihydrate M.p. 90–115° C. Mass spectrum 462 ($M^{+1}$). Elemental analysis calculated for $C_{23}H_{25}N_3OSCl_2.2\ HCl.2\ H_2O$: C, 51.64, H, 5.65, N, 7.86. Found: C, 51.83, H, 5.76, N 7.64.

EXAMPLE 6

5-[2-(4-Methylpiperazin-1-yl)-benzylidene]-thiazolidine-2,4-dione Hemihydrate

Yellow solid, m.p.105° C. (dec.). Mass spectrum 304 ($M^{+1}$). Elemental analysis calculated for $C_{15}H_{17}N_3O_2S.0.5\ H_2O$: C, 57.67, H, 5.81, N, 13.45. Found: C, 57.81, H, 6.48, N, 13.20. $^1$H-NMR ($CDCl_3$, 400 MHz) δ 8.05 (1H, s), 7.68 (1H, d), 7.36 (1H, dt), 7.12–7.03 (2H, m), 3.12–3.02 (5H, m), 2.71 (4H, br s), 2.41 (3H, s).

EXAMPLE 7

3-(4-Chlorophenyl)-5-[2-(4-methylpiperazin-1-yl)-benzyldene]-thiazolidine-2,4-dione Hydrochloride Hemihydrate Under a nitrogen atmosphere in a flame-dried flask, a mixture of 3-(4-chlorophenyl)-thiazolidine-2,4-dione (158 mg, 0.694 mmol), 2-(4-methylpiperazin-1-yl)-benzaldehyde (142 mg, 0.694 mmol) and sodium acetate (171 mg, 2.08 mmol) in 1 mL of glacial acetic acid was heated to reflux for approximately 6 hours and cooled to room temperature. Saturated aqueous sodium carbonate ($Na_2CO_3$) was added until the pH was about 10 and the mixture was extracted several times with methylene chloride. The organic layers were washed with brine, saturated sodium chloride, dried and evaporated to a brown solid which was recrystallized from ethyl acetate.

M.p. 187–189° C. Elemental analysis calculated for $C_{21}H_{20}N_3O_2ClS$: C, 60.94, H, 4.87, N, 10.15. Found: C, 60.57, H, 4.95, N, 10.00.

The above compound (56 mg) was treated with diethyl ether saturated with hydrogen chloride gas and the product was recrystallized from hot ethanol to yield 3-(4-chlorophenyl)-5-[2-(4-methylpiperazin-1-yl)-benzylidene]-thiazolidine-2,4-dione hydrochloride hemihydrate as a solid, 54 mg, m.p. 254–258° C.

Elemental analysis calculated for $C_{21}H_{20}N_3O_2ClS.HCl.0.5\ H_2O$: C, 54.90, H, 4.83, N, 9.15. Found: C, 55.07, H, 5.01, N, 8.78. $^1$H-NMR (DMSO-$d_6$) δ 10.84 (1H, br s), 7.60 (2H, d), 7.52–7.45 (4H, m), 7.24 (2H, t), 3.53–3.05 (8H, m), 2.80 (3H, s).

The following examples were prepared by an analogous procedure to that of Example 7, except as indicated.

EXAMPLE 8

3-(4-[Trifluoromethyl]-phenyl)-5-[2-(4-methylpiperazin-1-yl)-benzylidene]-thiazolidine-2,4-dione Hydrochloride Dihydrate M.p. 159–177° C. Mass spectrum 448 ($M^{+1}$). Elemental analysis calculated for $C_{22}H_{20}N_3O_2SF_3.HCl.2\ H_2O$: C, 50.82, H, 4.85, N, 8.08. Found: C, 51.04, H, 4.66, N, 8.01.

EXAMPLE 9

2-[2-(4-Methylpiperazin-1-yl)-benzylidene]-4-(4-trifluoromethylphenyl)-thiomorpholin-3-one Hydrochloride Trihydrate M.p. 128–134° C. Mass spectrum 448 ($M^{+1}$). $^1$H-NMR (DMSO-$d_6$, 400 MHz) δ 10.66 (1H, br s), 7.79 (1H, s), 7.76 (2H, d), 7.66 (1H, d), 7.61 (2H, d), 7.34 (1H, t), 7.15–7.10 (2H, m), 4.14 (2H, m), 3.43 (2H, br s), 3.22 (2H, m), 3.21–3.00 (6H, m), 2.78 (3H, s).

EXAMPLE 10

2-[2-(4-Methylpiperazin-1-yl)-benzylidene]-thiomorpholin-3-one

Sodium hydride (930 mg, 23.3 mmol of 60% oil dispersion) was washed with hexanes under a nitrogen atmosphere and suspended in 100 mL of anhydrous THF. Thiomorpholin-3-one (1.0 g, 8.55 mmol) was added, followed immediately by 2-(4-methylpiperazin-1-yl)-benzaldehyde (1.58 g, 7.75 mmol). The reaction was then heated to reflux overnight, cooled to room temperature and concentrated in vacuo. The residue was dissolved in methylene chloride and washed with aqueous ammonium chloride ($NH_4Cl$) and saturated brine and then dried with $MgSO_4$. Purification using flash chromatography gave 2-{hydroxy-[2-(4-methylpiperazin-1-yl)phenyl]-methyl}-thiomorpholin-3-one as a white solid, m.p. 137–139° C. Mass spectrum 322 ($M^{+1}$).

A mixture of 190 mg (0.6 mmol) of the preceding intermediate in 25 mL of toluene was treated with 135 mg (0.71 mmol) of p-toluenesulfonic acid and refluxed overnight with a Dean-Stark condenser to collect the water which azeotroped. After cooling, the solvent was removed and the residue was dissolved in methylene chloride, washed with saturated aqueous sodium carbonate ($Na_2CO_3$) and saturated brine, dried with magnesium sulfate and concentrated in vacuo to a brown foam. The free base was crystallized from ethyl acetateihexanes to yield a crystalline solid.

M.p. 133–135° C.; mass spectrum 304 ($M^{+1}$). Elemental analysis calculated for $C_{16}H_{21}N_3OS$: C, 63.34, H, 6.98, N, 13.85. Found: C, 63.17, H, 7.12, N, 13.67.

The following examples were prepared by an analogous procedure to Example 10, except where indicated.

EXAMPLE 11

4-(3,4-Dichlorophenyl)-2-[2-fluoro-6-(4-methylpiperazin-1-yl)-benzylidene]-thiomorpholin-3-one M.p. 146–147° C. Mass spectrum 466 ($M^{+1}$), 468.

EXAMPLE 12

4-(3,4-Dichlorophenyl)-2-[2-(4-methylpiperazin-1-yl)-benzylidene]-morpholin-3-one M.p. 169–171° C. (decomp.). Mass spectrum 432 ($M^{+1}$), 434, 436.

EXAMPLE 13

2-[2,4-Dibromo-6-(4-methylpiperazin-1-yl)-benzylidene]-4-(3,4-dlchlorophenyl)-thiomorpholin-3-one M.p. 166–168° C. Mass spectrum 607 ($M^{+1}$). Elemental analysis calculated for $C_{22}H_{21}N_3OSBr_2$: C, 43.59, H, 3.49, N, 6.93. Found: C, 43.56, H, 3.25, N, 6.89.

EXAMPLE 14

4-(3,4-Dichlorophenyl)-2-[2-(4-methylpiperazin-1-yl)-benzylidene]-thiomorpholin-3one M.p. 171–173° C. Mass spectrum 448 ($M^{+1}$).

Converting to the hydrochloride salt, using 1.0M HCl in ether, and recrystallizing from isopropanol gave pale yellow crystals.

M.p. 155–157° C. Elemental analysis calculated for $C_{22}H_{23}N_3OSCl_2 \cdot HCl \cdot 1.5H_2O$: C, 51.62, H, 5.32, N, 8.21. Found: C, 51.81, H, 5.02, N, 8.45.

EXAMPLE 15

4-(3,4-Dichlorophenyl)-2-[2-(4-methylpiperazin-1-yl)-benzyl-thiomorpholin-3-one Hydrochloride Trihydrate A slurry of 4-(3,4-dichlorophenyl)-2-[2-(4-methyl-piperazin-1-yl)-benzylidene]-thiomorpholin-3-one in (201 mg, 0.5 mmol) 3 mL of anhydrous methanol (3 ml) was treated with samarium iodide ($SmI_2$) (15 ml of 0.1 m) in THF (Aldrich Chemical Co., Milwaukee, Wis.) and stirred overnight at room temperature under a nitrogen atmosphere. An additional 5 mL of $SmI_2$ solution was added and, after an additional one hour, the solvent was removed in vacuo and the residue was flash chromatographed using ethyl acetate/methanol to elute the free base of the product. The hydrochloride salt was prepared, using 1.0M HCl in ether, to produce a light tan solid.

M.p. 105–110° C. (foam). Elemental analysis calculated for $C_{22}H_{25}N_3OSCl_2 \cdot HCl \cdot 3H_2O$: C, 48.85, H, 5.96, N, 7.77. Found: C, 48.95, H, 5.58, N, 7.51. $^1$H-NMR (CDCl$_3$, 400 MHz, free base) δ 7.45–7.41 (2H, m), 7.17–7.13 (2H, m), 7.06 (1H, t), 4.16 (1H, m), 4.00–3.86 (2H, m), 3.53 (1H, dd), 3.10–2.95 (7H, m) 2.61 (4H, br s), 2.37 (3H, s).

EXAMPLE 16

4-Methyl-2-[2-(4-methylpiperazin-1-yl)-benzylidene]-thiomorpholin-3-one Hydrochloride Hemihydrate Under a nitrogen atmosphere, sodium hydride (49 mg, 1.24 mmol, 60% oil dispersion) was washed with hexanes and layered with 6 mL of anhydrous THF. After cooling to 0° C., 2-[2-(4-methylpiperazin-1-yl)-benzylidene]-thiomorpholin-3-one (250 mg, 0.825 mmol) was added and the reaction was stirred for 30 min. To the resulting solution was added iodomethane (62 μL, 0.99 mmol), followed 15 minutes later by an additional 10 μL of iodomethane. After 30 min., the solvent was removed in vacuo and the residue was dissolved in methylene chloride and washed with aqueous ammonium chloride and aqueous brine. After drylng, the solvent was removed in vacuo and the residue was purified by flash chromatography. The free base was converted into the hydrochloride salt as described in Example 15 to produce the title product as a pale yellow solid.

M.p. 236–238° C. Mass spectrum 318 ($M^{+1}$). $^1$H-NMR (DMSO-d$_6$+D$_2$O 400 MHz) δ 7.70 (1H, s), 7.48 (1H, d), 7.30 (1H, t), 7.11–7.04 (2H, m), 3.69 (2H, br s), 3.55–3.30 (2H, br s), 3.29–3.02 (4H, m), 2.97 (3H, s), 2.90 (4H, br s), 2.79 (3H, s). Elemental analysis calculated for $C_{17}H_{23}N_3OS \cdot HCl \cdot 0.5 H_2O$: C, 56.26, H, 6.94, N, 11.58. Found: C, 56.22, H, 7.11, N, 11.37.

EXAMPLE 17

4-(3,4-Dichlorophenyl)-2-(2-piperazin-1-ylbenzylidene)-thiomorpholin-3-one

Under a nitrogen atmosphere, a mixture of 4-(3,4-dichlorophenyl)-2-[2-(4-methylpiperazin-1-yl)-benzylidene]-thiomorpholin-3-one (338 mg, 0.756 mmol) in 9 mL of anhydrous 1,2-dichloroethane was treated with α-chloroethyl chlorofonnate (98 μL 0.907 mmol) and refluxed overnight. The solvent was then removed in vacuo and 10 mL of methanol was added and refluxed for 30 minutes. Following removal of the solvent, the residue was extracted into methylene chloride and washed with saturated aqueous sodium carbonate ($Na_2CO_3$) and saturated brine, dried with magnesium sulfate and concentrated to a foam. Flash chromatography using triethyl amine/methanol/ethyl acetate (1:2:97) gave the purified free base of the title compound.

M.p. 198–200° C. Mass spectrum 434 ($M^{+1}$), 436. Elemental analysis calculated for $C_{21}H_{21}N_3OSCl_2$: C, 58.07, H, 4.87, N, 9.67. Found: C, $57.93$, H, 4.71, N, 9.43. Conversion to the hydrochloride salt using 1M HCl in CH$_3$OH, followed by recrystallization from isopropanol, gave a crystalline solid, m.p. 154–155° C.

PREPARATION 1

2-(4-Methylpiperazin-1-yl)-benzaldehyde

This compound was prepared using the methods of W. Nijhuis et al, *Synthesis*, 641–645 (1987) or J. Watthey et al, *Journal of Medicinal Chemistry*, 26, 1116–1122 (1983).

In the same manner as the preparation of 2-(4-methylpiperazin-1-yl)-benzaldehyde, the following analogs were also prepared:

4,6-Dibromo-2-(4-methylpiperazin-1-yl)-benzaldehyde

72% yleld. M.p. 92–93° C. Mass spectrum 362. $^1$H-NMR (CDCl$_3$, 250 MHz) δ 10.12 (1H, s), 7.44 (1H, d), 7.16 (1H, d), 3.10 (4H, br s), 2.61 (4H, s), 2.36 (3H, s).

6-Fluoro-2-(4-methylpiperazin-1-yl)-benzaldehyde

69% yield. Light brown oil. Mass spectrum 223 ($M^{+1}$). $^1$H-NMR (CDCl$_3$, 250 MHz) δ 10.27 (1H, s), 7.45 (1H, m), 7.86 (1H, d), 6.75 (1H, dd), 3.14 (4H, t), 2.62 (4H, t), 2.62 (4H, t), 2.37 (3H, s).

PREPARATION 2

2,4-Dibromo-6-fluoro-benzaldehyde

In a flame-dried 250 mL round-bottomed flask equipped with an addition funnel and magnetic stirrer, a mixture of diisopropylamine (4.82 mL, 34.66 mmol) in 100 mL of anhydrous THF was cooled to −78° C. and treated with 2.5N n-butyllithium (13.86 mL, 34.66 mmol) in THF, dropwise. After stirring for 10 minutes a mixture of 3,5-dibromo-1-fluorobenzene (8.0 g, 31.51 mmol) in 16 mL of THF was added dropwise and stirring was continued for an additional 30 minutes. At this point, N,N-dimethylformamide (DMF) (2.68 mL, 34.66 mmol) was added dropwise and stirring continued another 10 minutes at −78° C. The reaction was quenched with saturated aqueous ammonium chloride and the solvent removed on a rotary evaporator. The residue was dissolved in ether, washed with saturated brine and dried over calcium sulfate, filtered and concentrated to an oil, 7.36 g. Purification by flash chromatography using ethyl acetate-hexanes (1:99) gave the title product as a white solid.

M.p. 57–58° C. Mass spectrum 281 ($M^{+1}$), 283. $^1$H-NMR (CDCl$_3$, 400 MHz) δ 10.29 (1H, s), 7.66 (1H, t), 7.33 (1H, dd). Elemental analysis calculated for C$_7$H$_3$Br$_2$FO: C, 29.82, H, 1.07. Found: C, 30.25, H, 1.03.

PREPARATION 3

3-(4-Chlorobenzyl)-imidazolidine-2,4-dione

Under a nitrogen atmosphere in a flame-dred flask, with magnetic stirring, the potassium salt of imidazolidine-2,4-dione (1.382 g, 10 mmol) and 4-chlorobenzyl bromide (2.055 g, 10 mmol) were combined with 15 mL of anhydrous N,N-dimethylformamide (DMF) and heated to 170–175° C. for 5 hours. The reaction was then cooled to room temperature and poured over 50 mL of water to produce a waxy white precipitate. Recrystallization from ethyl acetate: hexanes produced the title product as a white crystalline solid, 0.775 g (34.5%).

M.p. 162–163.5° C. (dec.). $^1$H-NMR (DMSO-d$_6$) δ 8.17 (1H, s), 7.34 (4H, q), 4.51 (2H, s), 3.98 (2H, s), 3.35 (HOD, s).

In the same manner, the potassium salt of thiazolidine-2,4-dione (1.0 g. 6.45 mmol) was converted to 3-(4-chlorobenzyl)-thiazolidine-2,4-dione 0.97 g (62%).

$^1$H-NMR (CDCl$_3$, 250 MHz) δ 7.32 (4H, sym m), 4.73 (2H, 2), 3.95 (2H, s).

PREPARATION 4

4-(3,4-Dichlorophenyl)-thiomorpholin-3-one

Under a nitrogen atmosphere in a flame-dried flask, sodium hydride (72 mg, 1.79 mmol, 60% oil dispersion) was washed with hexanes and then treated with 6 mL of anhydrous DMF, and cooled to 0° C. Thiomorpholin-3-one (200 mg, 1.71 mmol) was added in one portion with stirring. After gas evolution had stopped (ca. 30 min), 4-iodo-1,2-dichlorobenzene (700 mg, 2.56 mmol) was added, followed after 5 minutes by copper (I) bromide (490 mg, 3.42 mmol). After heating at 75° C. overnight, the mixture was partitioned between ethyl acetate and 1N lithium chloride, filtered through diatomaceous earth and combined with additional ethyl acetate washes of the diatomaceous earth filter cake. The organic layers were washed with additional 1N lithium chloride, brine (saturated sodium chloride) and dried over calcium sulfate (CaSO4). Concentration in vacuo gave 363 mg of light brown oil which was flash chromatographed (30–50% ethyl acetate in hexanes) to give a white solid, 108 mg.

$^1$H-NMR (CDCl$_3$, 400 MHz) δ 7.44 (1H, d), 7.37 (1H, s), 7.12 (1H, dd), 3.93 (2H, t), 3.43 (2H, s), 3.01 (2H, t).

PREPARATION 5

4-(4-Trifluoromethylphenyl)-thiomorpholin-3-one

A mixture of thiomorpholin-3-one (500 mg, 4.27 mmol), 4-trifluoromethyl-1-iodobenzene (1.25 mL, 8.5 mmol) and copper metal (814 mg, 12.8 mmol) was heated in a sealed glass tube at 185–200° C. for 18 hours. The residue was then purified by flash chromatography to give 260 mg of the title product as a white solid.

M.p. 85–87° C. Mass spectrum 262 ($M^{+1}$). $^1$H-NMR (CDCl$_3$, 400 MHz) δ 7.62 (2H, d), 7.37 (2H, d), 3.97 (2H, t), 3.43 (2H, s), 3.01 (2H, t).

In the same manner, 4-(3,4-dichlorophenyl)-thiomorpholin-3-one was prepared using copper bronze (Aldrich Chemical Co., Milwaukee, Wis.) and heating in a round bottomed flask under nitrogen atmosphere at 170° in 37–46% isolated yield, m.p. 79–80° C.

PREPARATION 6

4-Benzylthiomorpholin-3-one

Under a nitrogen atmosphere in a flame-dried flask, sodium hydride (4.65 g, 0.105 mol, 54% oil dispersion) was added to 150 mL of anhydrous dimethylformamide (DMF), and the suspension was cooled to 0° C. Thiomorpholin-3-one (11.7 g, 0.1 mol) was added in portions over 30 minutes with stirring. After gas evolution had stopped (ca. 30 minutes), benzyl chloride (12.1 g, 0.105 mol) in DMF (50 mL) was added and stirring was continued at room temperature overnight. The reaction was then warmed to 80° C. for 15 minutes and cooled. Water (250 mL) was added and the mixture was extracted with chloroform which was dried (MgSO$_4$) and concentrated in vacuo to an oil. The oil was triturated with ethyl ether (Et$_2$O) and cooled by dry ice to give the product, 12.75 g as a solid, m.p. 60–62° C.

Recrystallization of 5 g from 100 mL of Et$_2$O gave 3.5 g of pure product, m.p. 62–63° C. along with a second crop of 0.75 g with m.p. 62–63° C.

In the same manner, 4-(3,4-dichlorobenzyl)-thiomorpholin3-one was prepared in 89% yleld from 3,4-dichlorobenzyl bromide and thiomorpholin-3-one as a white solid.

M.p. 86–87° C. $^1$H-NMR (CDCl$_3$, 400 MHz) δ 7.38 (1H, d), 7.33 (1H, d), 7.10 (1H, dd), 4.56 (2H, s), 3.55–3.51 (2H, m), 3.37 (2H, s), 2.81–2.76 (2H, m).

What is claimed is:

1. A method for preventing depression in a mammal comprising administering to a mammal in need of such prevention an amount of a compound of formula I

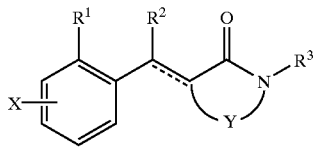

wherein R¹ is a group of the formula G¹, G², G³, G⁴, G⁵, G⁶ or G⁷ depicted below,

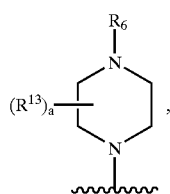

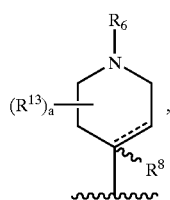

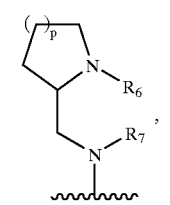

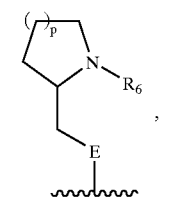

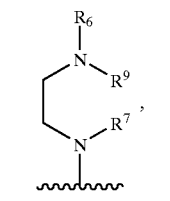

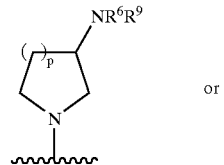

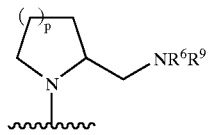

a is zero to eight;

each $R^{13}$ is, independently a $(C_1-C_4)$alkylene bridge from one of the ring carbons of the piperazine ring of $G^1$ to the same or another ring carbon of the piperazine ring of $G^1$ or to a ring nitrogen of the piperazine ring of $G^1$ when said ring carbon or ring nitrogen has an available bonding site, or when $R^6$ has a ring structure having an available bonding site, to a ring carbon of $R^6$, or a $(C_1-C_4)$alkylene bridge from one of the ring carbons of the piperidine ring of $G^2$ to the same or another ring carbon of the piperidine ring of $G^2$ or to the ring nitrogen of the piperidine ring of $G^2$, when said ring carbon or ring nitrogen has an available bonding site, or when $R^6$ has a ring structure having an available bonding site, to a ring carbon of $R^6$;

E is oxygen, sulfur, SO or $SO_2$;

X is hydrogen, chloro, fluoro, bromo, iodo, cyano, $(C_1-C_6)$alkyl, hydroxy, trifluoromethyl, $(C_1-C_6)$ alkoxy, $-SO_t(C_1-C_6)$alkyl wherein t is zero one or two, $-CO_2R^{10}$ or $-CONR^{11}R^{12}$;

Y is an optionally substituted heteroalkyl bridge that, together with the atoms to which it is attached, forms a six-membered heterocycle selected from the group consisting of thiomorpholin-3-on-2-yl, thiomorpholin-3,5-dion-2-yl, 1-oxo-thiomorpholin-3-on-2-yl, and 1,1-dioxothiomorpholin-3-on-2-yl wherein the substituents on any of the carbon atoms capable of supporting an additional bond, of said heteroalkyl bridge, are chloro, fluoro, $(C_1-C_6)$alkyl, $(C_1-C_6)$alkoxy, trifluoromethyl or cyano;

$R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and $-SO_k(C_1-C_6)$alkyl wherein k is zero, one or two;

$R^3$ is $-(CH_2)_mB$, wherein m is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$alkoxy-$(C_1-C_6)$alkyl-, trifluoromethyl, trifluoromethoxy, cyano, hydroxy, $-COOH$ and $-SO_n(C_1-C_6)$alkyl wherein n is zero, one or two;

$R^6$ is selected from the group consisting of hydrogen, $(C_1-C_6)$alkyl optionally substituted with $(C_1-C_6)$ alkoxy or one to three fluorine atoms, or $((C_1-C_4)$ alkyl)aryl wherein the aryl moiety is phenyl, naphthyl, or heteroaryl-$(CH_2)_q-$, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_g(C_1-C_6)$alkyl, wherein g is zero, one or two;

$R^7$ is selected from the group consisting of hydrogen, $(C_1-C_6)$alkyl, $((C_1-C_4)$alkyl)aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, —C(=O)—$(C_1-C_6)$alkyl, cyano and —$SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^6$ and $R^9$, together with the nitrogen atom to which they are attached, form a 5 to 7 membered heteroalkyl ring that may contain from zero to four heteroatoms selected from nitrogen, sulfur and oxygen;

and p is one, two, or three;

each of $R^{10}$, $R^{11}$ and $R^{12}$ is selected, independently, from the radicals set forth in the definition of $R^2$; or $R^{11}$ and $R^{12}$, together with the nitrogen to which they are attached, form a 5 to 7 membered heteroalkyl ring that may contain from zero to four heteroatoms selected from nitrogen, sulfur and oxygen; and the broken lines indicate optional double bonds, with the proviso that when the broken line in $G^2$ is a double bond that $R^8$ is absent;

or a pharmnaceutically acceptable salt thereof that is effective in preventing such disorder or condition.

2. A method for preventing depression in a mammal comprising administering to a mammal in need of such prevention a serotonin receptor antagonizing or agonizing effective amount of a compound of formula I

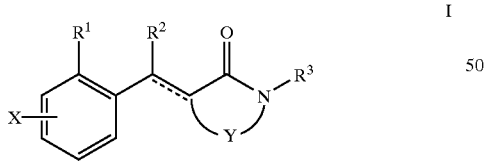

I wherein $R^1$ is a group of the formula $G^1$, $G^2$, $G^3$, $G^4$, $G^5$, $G^6$ or $G^7$ depicted below,

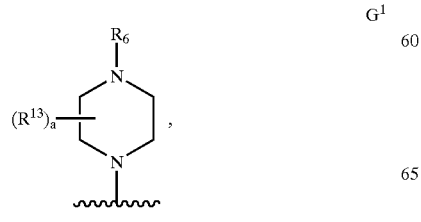

G¹

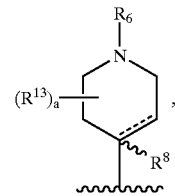

G²

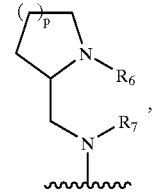

G³

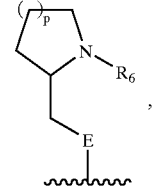

G⁴

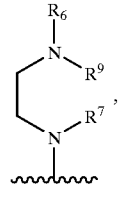

G⁵

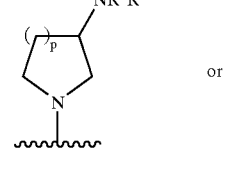

G⁶

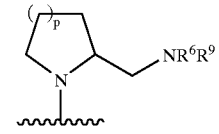

or

G⁷ a is zero to eight;

each $R^{13}$ is, independently, a $(C_1-C_4)$alkylene bridge from one of the ring carbons of the piperazine ring of $G^1$ to the same or another ring carbon of the piperazine ring of $G^1$ or to a ring nitrogen of the piperazine ring of $G^1$ when said ring carbon or ring nitrogen has an available bonding site, or when $R^6$ has a ring structure having an available bonding site, to a ring carbon of $R^6$, or a $(C_1-C_4)$alkylene bridge from one of the ring carbons of the piperidine ring of $G^2$ to the same or another ring carbon of the piperidine ring of $G^2$ or to the ring nitrogen of the piperidine ring of $G^2$, when said ring carbon or ring nitrogen has an available bonding site, or when $R^6$ has a ring structure having an available bonding site, to a ring carbon of $R^6$;

E is oxygen, sulfur, SO or $SO_2$;

X is hydrogen, chloro, fluoro, bromo, iodo, cyano, $(C_1-C_6)$alkyl, hydroxy, trifluoromethyl, $(C_1-C_6)$alkoxy, —$SO_t(C_1-C_6)$alkyl wherein t is zero one or two, —$CO_2R^{10}$ or —$CONR^{11}R^{12}$;

Y is an optionally substituted heteroalkyl bridge that, together with the atoms to which it is attached, forms a six-membered heterocycle selected from the group consisting of thiomorpholin-3-on-2-yl, thiomorpholin-3,5-dion-2-yl, 1-oxo-thiomorpholin-3-on-2-yl, and 1,1-dioxothiomorpholin-3-on-2-yl wherein the substituents on any of the carbon atoms capable of supporting an additional bond, of said heteroalkyl bridge, are chloro, fluoro, $(C_1-C_6)$alkyl, $(C_1-C_6)$alkoxy, trifluoromethyl or cyano;

$R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and —$SO_k(C_1-C_6)$alkyl wherein k is zero, one or two;

$R^3$ is —$(CH_2)_mB$, wherein m is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$alkoxy-$(C_1-C_6)$alkyl-, trifluoromethyl, trifluoromethoxy, cyano, hydroxy, —COOH and —$SO_n(C_1-C_6)$alkyl wherein n is zero, one or two;

$R^6$ is selected from the group consisting of hydrogen, $(C_1-C_6)$alkyl optionally substituted with $(C_1-C_6)$ alkoxy or one to three fluorine atoms, or $((C_1-C_4)$ alkyl)aryl wherein the aryl moiety is phenyl, naphthyl, or heteroaryl-$(CH_2)_q$—, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_g(C_1-C_6)$alkyl, wherein g is zero, one or two;

$R^7$ is selected from the group consisting of hydrogen, $(C_1-C_6)$alkyl, $((C_1-C_4)$alkyl)aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, —C(=O)—$(C_1-C_6)$alkyl, cyanpo and —$SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^6$ and $R^9$, together with the nitrogen atom to which they are attached, form a 5 to 7 membered heteroalkyl ring that may contain from zero to four heteroatoms selected from nitrogen, sulfur and oxygen;

and p is one, two, or three;

each of $R^{10}$, $R^{11}$ and $R^{12}$ is selected, independently, from the radicals set forth in the definition of $R^2$; or $R^{11}$ and $R^{12}$, together with the nitrogen to which they are attached, form a 5 to 7 membered heteroalkyl ring that may contain from zero to four heteroatoms selected from nitrogen, sulfur and oxygen; and the broken lines indicate optional double bonds, with the proviso that when the broken line in $G^2$ is a double bond that $R^8$ is absent;

or a pharmaceutically acceptable salt thereof.

3. A method for preventing depression in a mammal comprising administering to a mammal in need of such prevention:

a) a compound of formula I

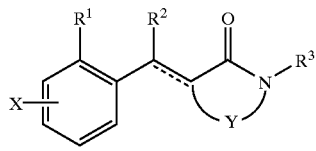

wherein $R^1$ is a group of the formula $G^1$, $G^2$, $G^3$, $G^4$, $G^5$, $G^6$ or $G^7$ depicted below,

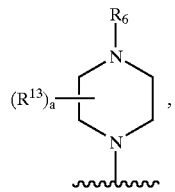

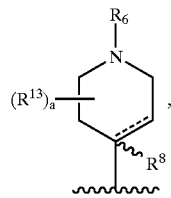

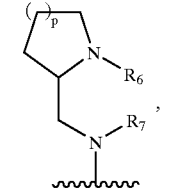

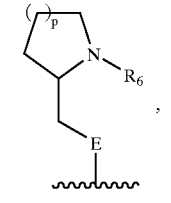

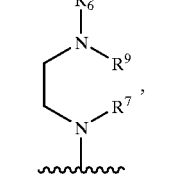

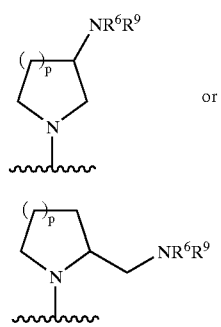

a is zero to eight;

each $R^{13}$ is, independently a $(C_1-C_4)$alkylene bridge from one of the ring carbons of the piperazine ring of $G^1$ to the same or another ring carbon of the piperazine ring of $G^1$ or to a ring nitrogen of the piperazine ring of $G^1$ when said ring carbon or ring nitrogen has an available bonding site, or when $R^6$ has a ring structure having an available bonding site, to a ring carbon of $R^6$, or a $(C_1-C_4)$alkylene bridge from one of the ring carbons of the piperidine ring of $G^2$ to the same or another ring carbon of the piperidine ring of $G^2$ or to the ring nitrogen of the piperidine ring of $G^2$, when said ring carbon or ring nitrogen has an available bonding site, or when $R^6$ has a ring structure having an available bonding site, to a ring carbon of $R^6$;

E is oxygen, sulfur, SO or $SO_2$;

X is hydrogen, chloro, fluoro, bromo, iodo, cyano, $(C_1-C_6)$alkyl, hydroxy, trifluoromethyl, $(C_1-C_6)$alkoxy, $-SO_t(C_1-C_6)$alkyl wherein t is zero one or two, $-CO_2R^{10}$ or $-CONR^{11}R^{12}$;

Y is an optionally substituted heteroalkyl bridge that, together with the atoms to which it is attached, forms a six-membered heterocycle selected from the group consisting of thiomorpholin-3-on-2-yl, thiomorpholin-3,5-dion-2-yl, 1-oxo-thiomorpholin-3-on-2-yl, and 1,1-dioxothiomorpholin-3-on-2-yl wherein the substituents on any of the carbon atoms capable of supporting an additional bond, of said heteroalkyl bridge, are chloro, fluoro, $(C_1-C_6)$alkyl, $(C_1-C_6)$alkoxy, trifluoromethyl or cyano;

$R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and $-SO_k(C_1-C_6)$alkyl wherein k is zero, one or two;

$R^3$ is $-(CH_2)_mB$, wherein m is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$alkoxy-$(C_1-C_6)$alkyl-, trifluoromethyl, trifluoromethoxy, cyano, hydroxy, $-COOH$ and $-SO_n(C_1-C_6)$alkyl wherein n is zero, one or two;

$R^6$ is selected from the group consisting of hydrogen, $(C_1-C_6)$alkyl optionally substituted with $(C_1-C_6)$alkoxy or one to three fluorine atoms, or $((C_1-C_4)$alkyl)aryl wherein the aryl moiety is phenyl, naphthyl, or heteroaryl-$(CH_2)_q-$, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and $-SO_g(C_1-C_6)$alkyl, wherein g is zero, one or two;

$R^7$ is selected from the group consisting of hydrogen, $(C_1-C_6)$alkyl, $((C_1-C_4)$alkyl)aryl wherein the aryl moiety is phenyl, naphthyl, or heteroaryl-$(CH_2)_r-$, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, $-C(=O)-$$(C_1-C_6)$alkyl, cyano and $-SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^6$ and $R^9$, together with the nitrogen atom to which they are attached, form a 5 to 7 membered heteroalkyl ring that may contain from zero to four heteroatoms selected from nitrogen, sulfur and oxygen;

and p is one, two, or three;

each of $R^{10}$, $R^{11}$ and $R^{12}$ is selected, independently, from the radicals set forth in the definition of $R^2$; or $R^{11}$ and $R^{12}$, together with the nitrogen to which they are attached, form a 5 to 7 membered heteroalkyl ring that may contain from zero to four heteroatoms selected from nitrogen, sulfur and oxygen; and the broken lines indicate optional double bonds, with the proviso that when the broken line in $G^2$ is a double bond that $R^8$ is absent;

or a pharmaceutically acceptable salt thereof; and b) a serotonin re-uptake inhibitor or a pharmaceutically acceptable salt thereof;

wherein the amounts of the active compounds are such that the combination is effective in preventing such disorder or condition.

4. A method according to claim 3 herein the serotonin re-uptake inhibitor is sertraline or a pharmaceutically acceptable salt thereof.

5. A method for preventing depression in a mammal comprising administering to a mammal in need of such prevention:

a) a serotonin-1A receptor antagonist or a pharmaceutically acceptable salt thereof; and b) a serotonin-1D receptor antagonist of formula I

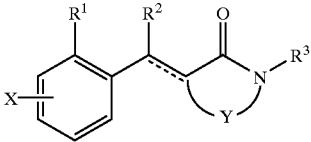

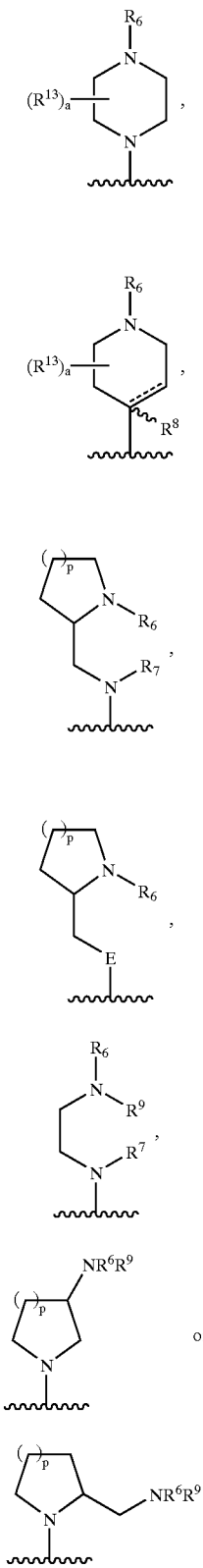

wherein $R^1$ is a group of the formula $G^1$, $G^2$, $G^3$, $G^4$, $G^5$, $G^6$ or $G^7$ depicted below, a is zero to eight;
each $R^{13}$ is, independently a $(C_1-C_4)$alkylene bridge from one of the ring carbons of the piperazine ring of $G^1$ to the same or another ring carbon of the piperazine ring of $G^1$ or to a ring nitrogen of the piperazine ring of $G^1$ when said ring carbon or ring nitrogen has an available bonding site, or when $R^6$ has a ring structure having an available bonding site, to a ring carbon of $R^6$, or
a $(C_1-C_4)$alkylene bridge from one of the ring carbons of the piperidine ring of $G^2$ to the same or another ring carbon of the piperidine ring of $G^2$ or to the ring nitrogen of the piperidine ring of $G^2$, when said ring carbon or ring nitrogen has an available bonding site, or when $R^6$ has a ring structure having an available bonding site, to a ring carbon of $R^6$;
E is oxygen, sulfur, SO or $SO_2$;
X is hydrogen, chloro, fluoro, bromo, iodo, cyano, $(C_1-C_6)$alkyl, hydroxy, trifluoromethyl, $(C_1-C_6)$alkoxy, $—SO_t(C_1-C_6)$alkyl wherein t is zero one or two, $—CO_2R^{10}$ or $—CONR^{11}R^{12}$;
it is Y is an optionally substituted heteroalkyl bridge that, together with the atoms to which it is attached, forms a six-membered heterocycle selected from the group consisting of thiomorpholin-3-on-2-yl, thomorpholin-3,5-dion-2-yl, 1-oxo-thiomorpholin-3-on-2-yl, and 1,1-dioxothiomorpholin-3-on-2-yl wherein the substituents on any of the carbon atoms capable of supporting an additional bond, of said heteroalkyl bridge, are chloro, fluoro, $(C_1-C_6)$alkyl, $(C_1-C_6)$alkoxy, trifluoromethyl or cyano;
$R^2$ is hydrogen, $(C_1-C_4)$alkyl, phenyl or naphthyl, wherein said phenyl or naphthyl may optionally be substituted with one or more substituents independently selected from chloro, fluoro, bromo, iodo, $(C_1-C_6)$alkyl, $(C_1-C_6)$alkoxy, trifluoromethyl, cyano and $—SO_k(C_1-C_6)$alkyl wherein k is zero, one or two;
$R^3$ is $—(CH_2)_mB$, wherein m is zero, one, two or three and B is hydrogen, phenyl, naphthyl or a 5 or 6 membered heteroaryl group containing from one to four heteroatoms in the ring, and wherein each of the foregoing phenyl, naphthyl and heteroaryl groups may optionally be substituted with one or more substituents independently selected from chloro, fluoro, bromo, iodo, $(C_1-C_6)$alkyl, $(C_1-C_6)$alkoxy, $(C_1-C_6)$alkoxy-$(C_1-C_6)$alkyl-, trifluoromethyl, trifluoromethoxy, cyano, hydroxy, —COOH and $—SO_n(C_1-C_6)$alkyl wherein n is zero, one or two;
$R^6$ is selected from the group consisting of hydrogen, $(C_1-C_6)$alkyl optionally substituted with $(C_1-C_6)$alkoxy or one to three fluorine atoms, or $((C_1-C_4)$alkyl)aryl wherein the aryl moiety is phenyl, naphthyl, or heteroaryl-$(CH_2)_q—$, wherein the heteroaryl moiety is selected from the group consisting of pyridyl, pyrimidyl, benzoxazolyl, benzothiazolyl, benzisoxazolyl and benzisothiazolyl and q is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, cyano and —$SO_g(C_1-C_6)$alkyl, wherein g is zero, one or two;

$R^7$ is selected from the group consisting of hydrogen, $(C_1-C_6)$alkyl, $((C_1-C_4)$alkyl)aryl wherein the aryl moiety is phenyl, naphthyl, or heteroaryl-$(CH_2)_r$—, wherein the heteroaryl moiety is selected from the group consisting of pyridyl, pyrimidyl, benzoxazolyl, benzothiazolyl, benzisoxazolyl and benzisothiazolyl and r is zero, one, two, three or four, and wherein said aryl and heteroaryl moieties may optionally be substituted with one or more substituents independently selected from the group consisting of chloro, fluoro, bromo, iodo, $(C_1-C_6)$alkyl, $(C_1-C_6)$alkoxy, trifluoromethyl, —C(=O)—$(C_1-C_6)$alkyl, cyano and —$SO_j(C_1-C_6)$alkyl, wherein j is zero, one or two;

or $R^6$ and $R^7$ taken together form a 2 to 4 carbon chain;

$R^8$ is hydrogen or $(C_1-C_3)$alkyl;

$R^9$ is hydrogen or $(C_1-C_6)$alkyl;

or $R^6$ and $R^9$, together with the nitrogen atom to which they are attached, form a 5 to 7 membered heteroalkyl ring that may contain from zero to four heteroatoms selected from nitrogen, sulfur and oxygen;

and p is one, two, or three;

each of $R^{10}$, $R^{11}$ and $R^{12}$ is selected, independently, from the radicals set forth in the definition of $R^2$; or $R^{11}$ and $R^{12}$, together with the nitrogen to which they are attached, form a 5 to 7 membered heteroalkyl ring that may contain from zero to four heteroatoms selected from nitrogen, sulfur and oxygen; and the broken lines indicate optional double bonds, with the proviso that when the broken line in $G^2$ is a double bond that $R^8$ is absent;

or a pharmaceutically acceptable salt thereof;

wherein the amounts of the active compounds are such that the combination is effective in preventing such disorder or condition.

* * * * *